United States Patent
Bingaman et al.

(10) Patent No.: US 10,307,404 B1
(45) Date of Patent: *Jun. 4, 2019

(54) OCULAR FORMULATIONS FOR DRUG-DELIVERY TO THE POSTERIOR SEGMENT OF THE EYE

(71) Applicant: PanOptica, Inc., Bernardsville, NJ (US)

(72) Inventors: David P. Bingaman, Weatherford, TX (US); Paul G. Chaney, Mount Arlington, NJ (US); Martin B. Wax, Far Hills, NJ (US)

(73) Assignee: PanOptica, Inc., Mount Arlington, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/042,003

(22) Filed: Jul. 23, 2018

Related U.S. Application Data

(63) Continuation of application No. 14/775,357, filed as application No. PCT/US2014/027589 on Mar. 14, 2014, now Pat. No. 10,092,549.

(60) Provisional application No. 61/784,681, filed on Mar. 14, 2013.

(51) Int. Cl.
| | |
|---|---|
| *A01N 43/80* | (2006.01) |
| *A61K 31/425* | (2006.01) |
| *A61K 31/427* | (2006.01) |
| *A61K 9/08* | (2006.01) |
| *A61K 47/18* | (2017.01) |
| *A61K 9/00* | (2006.01) |
| *A61K 47/40* | (2006.01) |

(52) U.S. Cl.
CPC .......... *A61K 31/427* (2013.01); *A61K 9/0048* (2013.01); *A61K 9/08* (2013.01); *A61K 47/18* (2013.01); *A61K 47/186* (2013.01); *A61K 47/40* (2013.01)

(58) Field of Classification Search
None
See application file for complete search history.

(56) References Cited

U.S. PATENT DOCUMENTS

| | | | |
|---|---|---|---|
| 5,891,913 A * | 4/1999 | Sallmann | A61K 31/196 514/567 |
| 6,235,764 B1 | 5/2001 | Larson et al. | |
| 6,254,860 B1 | 7/2001 | Garst | |
| 7,749,970 B2 | 7/2010 | Dawson et al. | |
| 2002/0151573 A1 | 10/2002 | Gant | |
| 2005/0074497 A1 * | 4/2005 | Schultz | A61K 9/0048 424/486 |
| 2005/0234018 A1 | 10/2005 | Lyons et al. | |
| 2006/0292203 A1 | 12/2006 | Dellamary et al. | |
| 2007/0020336 A1 * | 1/2007 | Loftsson | A61K 9/0043 424/486 |
| 2008/0280890 A1 | 11/2008 | Patil | |
| 2009/0304694 A1 | 12/2009 | Oliner et al. | |

FOREIGN PATENT DOCUMENTS

| | | |
|---|---|---|
| JP | H10203960 A | 8/1998 |
| JP | 2006111621 A | 4/2006 |
| JP | 2010265261 A | 11/2010 |
| JP | 2012250918 A | 12/2012 |
| RU | 2008125986 A | 1/2010 |
| WO | WO 2001/017527 | 3/2001 |
| WO | WO 2004/011461 A1 | 2/2004 |

OTHER PUBLICATIONS

Shah et al. (Expert Rev Ophthalmo., May 2010, 75-93), (Year: 2010).*
Beebe JS, et al. "Pharmacological characterization of CP-547,632, a novel vascular endothelial growth factor receptor-2 tyrosine kinase inhibitor for cancer therapy", Cancer Research, vol. 63, 2003, p. 7301-7309.
Bingaman, D. P. et al., "AL-39324 is more potent and efficacious against ocular NV vs. other RTKi's", Investigative Ophthalmology & Visual Science, Dec. 31, 2007, vol. 48, pp. 1747-1748.
China Intellectual Property Yearbook 2008, p. 776.
Fleisher, D. et al., "Improved oral drug delivery: solubility limitations overcome by the use of prodrugs", Advanced Drug Delivery Reviews, vol. 19, (1996), pp. 115-130.
Handbook of Pharmaceutical Excipients, Rowe et al., 2002, pp. 516-519.
Ling Peixue Ophthalmic Drugs and Preparation Techniques, (2010), pp. 194-285.
Ling Peixue Ophthalmic Drugs and Preparation Techniques, (2010), pp. 109-124.
Loftsson, T. et al., "Cyclodextrins in eye drop formulations: enhanced topical delivery of corticosteroids to the eye", Acta Ophthalmologica Scandinavica, Apr. 1, 2002, vol. 80, No. 2, pp. 144-150.

(Continued)

*Primary Examiner* — Dennis Heyer
*Assistant Examiner* — Daniel M Podgorski
(74) *Attorney, Agent, or Firm* — Cooley LLP; Heidi A. Erlacher; Chen Chen

(57) ABSTRACT

The present invention relates to topical formulations comprising a compound of the following formula:

(Compound-I)

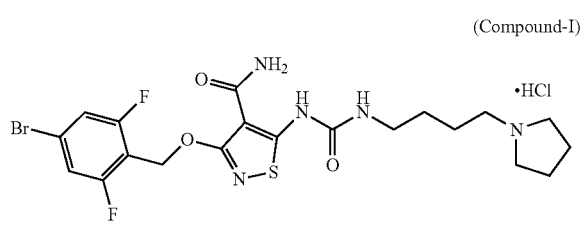

for treating ocular neovascularization. The Compound-I is present in a solution or a suspension in about 0.005% to about 5.0% w/v, such that the solution or suspension delivers the compound at the posterior segment of the eye for inhibiting VEGF in the retina and/or the choroid.

37 Claims, No Drawings

(56) References Cited

OTHER PUBLICATIONS

Loftsson, T., et al., "Pharmaceutical applications of cyclodextrins: basic science and product development", Journal of Pharmacy and Pharmacology, Jul. 20, 2010, vol. 62, No. 11, pp. 1607-1621.
Pharmaceutics I, Chen Changan, p. 205.
Robinson R. et al., "Discovery of the Hemifumarate and (α-L-Alanyloxy)methyl Ether as Prodrugs of an Antirheumatic Oxindole: Prodrugs for the Enolic OH Group", J. Med. Chem., vol. 39, (1996), pp. 10-18.
Shah et al. Expert Rev Ophthalmo, May 2010, p. 75-93.
Shi Haibo & Wang Kelin (ed.), A New 30 Handbook of Clinical Drugs, 3rd edition (Jan. 2013), pp. 458-459.
Shimpi, S. et al., "Cyclodextrins: application in different routes of drug administration", Acta Pharmaceutica, Dec. 31, 2005, vol. 55, No. 2, pp. 139-156.
Stella V. et al., "Cyclodextrins", Toxicologic Pathology, vol. 36, (2008), pp. 30-42.
Yao Jing (ed.), Application Directory of Pharmaceutical Excipients, (2011), pp. 279-281.
Zhao Jun et al (ed.), Eye Diseases Related to Diabetes, 20 (2009), pp. 82-92.

\* cited by examiner

OCULAR FORMULATIONS FOR DRUG-DELIVERY TO THE POSTERIOR SEGMENT OF THE EYE

RELATED APPLICATIONS

This application is a continuation of U.S. application Ser. No. 14/775,357, filed Sep. 11, 2015 (now allowed), which is a U.S. National Phase application, filed under 35 U.S.C. § 371, of International Application No. PCT/US2014/027589, filed Mar. 14, 2014, which claims priority to, and the benefit of, U.S. Provisional Application No. 61/784,681, filed Mar. 14, 2013, the entire contents of each of which are incorporated herein by reference.

FIELD OF INVENTION

Embodiments disclosed herein are generally directed to topical administration of a pharmaceutical compound or a salt thereof to treat ocular diseases or conditions. The embodiments disclosed include ocular formulations of a pharmaceutical compound or salt thereof, where the formulation is a solution or a suspension. The solution comprises a solubilizing agent, and is suitable for delivering to the posterior segment of the eye of a subject.

BACKGROUND

Treatment of diseases or disorders of the posterior segment of the eye with topically applied active agents has not been effective because of inefficient delivery of the active agent to the target site. The vast majority of topical drugs penetrate via the cornea. However, the cornea is not equally permeable to all topically applied active agents, since the basic structure of the cornea dictates the relative penetration of active agent. Effectively, the greatest barrier to active agent penetration is the corneal epithelium which is rich in cellular membranes and is therefore more susceptible to penetration by active agents which are lipophilic. In contrast, since the corneal stroma is largely constituted of water, active agents pass more readily through this thickest component of the cornea if they are hydrophilic. The endothelium represents a monolayer that, once more, is lipophilic. Active agents which are lipophilic or amphiphilic, in that they can behave as either charged or non-charged, penetrate the cornea best. Similar to the cornea, the conjunctival epithelium and blood vessels within or under the conjunctival epithelium may be penetrated by the same type of lipophilic or biphasic agents. However, because of the nature of the lipophilic membranes in the conjunctive and its inherent vasculature, most active agents typically do not penetrate through the conjunctiva and into the eye. Agents with limited penetration into the vascular tissues in the conjunctival and subconjunctival regions are drained into the systemic circulation.

If an active agent gains access through the cornea into the anterior chamber, barriers to successful drug delivery to posterior segment tissues such as the retina and choroid-still exist. These barriers consist of, at least in part, passive barriers such as aqueous humor flow dynamics, lens and lens zonules, and a large vitreous volume, as well as active barriers, such as cellular transporters or pumps located in the ciliary epithelium or in ionic gradients established in the eye.

Despite the challenges in delivering drugs topically to the posterior segment of the eye, there are several advantages of this route of administration over systemic delivery and over intravitreal or subconjunctival delivery. Intravitreal and subconjunctival injections typically rely on the use of a needle affixed to a syringe to penetrate either the wall of the eye or the conjunctival tissue to deliver aqueous pharmacological agents or aqueous suspensions of agents (e.g., steroids) for acute treatment. However it should also be noted that an increasing number of modalities can deliver sustained payload via vehicle devices such as polymers, organic cells, or nanoparticles to deliver the active agent therapeutic agent for a sustained or prolonged period of period of time. Topical delivery allows direct application to the target organ—the eye, with relative ease of application for the majority of patients, and due to targeted application, the need for smaller doses of the active agent associated with onset of action, often resulting in reduced or nonexistent systemic exposure. Disadvantages of topical delivery include: contamination of topical drops, the potential requirement for preservatives, the potential toxicity of the drug or the preservative to the ocular surface, the limitation of the penetration of most topical active agents via conjunctiva, cornea, and the anterior chamber, and the risk, although significantly smaller compared to systemic delivery, of systemic absorption of drugs which may act on other organs—such as the heart and lungs. Well-recognized complications of intravitreal injection include infection, retinal detachment, hemorrhage and scarring. The complications of subconjunctival injection also include infection, scarring, hemorrhage and inadvertent penetration of the globe.

Because of the limited permeability of many topical drops to the corneal and conjunctival barriers, one major disadvantage of topical drops, may be the need for high concentration of active agents in the topical formulation in order to achieve meaningful therapeutic drug levels in the eye. Depending on the active agent, the concentration in the topical formulation may be highly toxic to the anterior segment of the eye, including the cornea and lens. Therefore, treating diseases or disorders of the posterior segment of the eye would benefit from formulations that allow low bioavailability of the active agent at the anterior segment, while providing availability of an effective concentration of the active at the posterior segment.

The current embodiments provide novel formulations which circumvent the problems encountered in ocular delivery of existing topical therapeutic agents. The current invention accomplishes the combined effects of decreasing corneal and anterior segment drug exposure, while increasing posterior segment bioavailability. By lowering corneal exposure and increasing posterior segment bioavailability, the formulation of the current invention improves ocular tolerability and increases therapeutic index of the active agent.

SUMMARY OF THE INVENTION

The present invention relates to pharmaceutical formulations in form of a solution and/or a suspension, which lower exposure to the active agent in the anterior segment of the eye, for example the cornea, while increasing the bioavailability of the agent at the posterior segment of the eye, for example at the central choroid and/or the central retina.

The embodiments provide two distinct forms of formulation comprising the active agent, a solution and a suspension, with superior characteristics compared to another composition formed as a gel. The embodiments provide that the active agent formulated as a solution and/or a suspension are superior compared to when the same active ingredient is formulated as a gel form in delivering the active at the posterior segment of eye, while lowering the exposure in the front of the eye. Increased levels of the active agent in the front of the eye limit ocular tolerability of topical drops containing the active. Therefore, reduced bioavailability of the active agent at the corneal or conjunctival surface, while maintaining adequate concentrations necessary to bind the relevant receptors at the target tissues and confer a therapeutic effect in the posterior segment of the eye, such as the choroid and the retina, are highly desirable and are the outcomes achieved from the specific embodiments described here.

The present invention relates to formulations and methods useful for treating pathological states that arise or are exacerbated by ocular angiogenesis and vascular leakage, for example, in diabetic retinopathy (including background diabetic retinopathy, proliferative diabetic retinopathy and diabetic macular edema); age-related macular degeneration (AMD) (including neovascular (wet/exudative) AMD, dry AMD, and Geographic Atrophy); pathologic choroidal neovascularization (CNV) from any mechanism (i.e. high myopia, trauma, sickle cell disease; ocular histoplasmosis, angioid streaks, traumatic choroidal rupture, drusen of the optic nerve, and some retinal dystrophies); pathologic retinal neovascularization from any mechanism (i.e., sickle cell retinopathy, Eales disease, ocular ischemic syndrome, carotid cavernous fistula, familial exudative vitreoretinopathy, hyperviscosity syndrome, idiopathic occlusive arteriolitis, birdshot retinochoroidopathy, retinal vasculitis, sarcoidosis, or toxoplasmosis); uveitis; retinal vein occlusion (central or branch); ocular trauma; surgery induced edema; surgery induced neovascularization; cystoid macular edema; ocular ischemia; retinopathy of prematurity; Coat's disease; sickle cell retinopathy and/or neovascular glaucoma. The formulation of the current invention has, at least, one anti-angiogenic agent, anti-inflammatory agent, or anti-vascular permeability agent for use in treating angiogenic ocular disorders.

According to embodiments of the invention, the active agent is a kinase inhibitor. Examples of some kinase inhibitors that can be used to bring about beneficial therapeutic results include inhibitors of receptor tyrosine kinases, for example, without being limiting, VEGFR, FGFR, Tie-2, and Ephrin kinase receptors.

The embodiments of the current invention provide an ophthalmic formulation for treating ocular neovascularization with an active agent of Formula I:

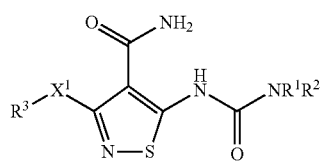

(I)

or a pharmaceutically acceptable salt thereof; and pharmaceutically acceptable excipients; the active agent or the pharmaceutically acceptable salt is present in about 0.02% to about 0.6% w/v such that the formulation forms a solution or suspension, and where the active agent is identified as: $X^1$ is O or S; $R^1$ is H, $C_1$-$C_{10}$ alkyl, $C_2$-$C_{10}$ alkenyl, $C_2$-$C_{10}$ alkynyl, —C(O)($C_1$-$C_{10}$ alkyl), —$(CH_2)_t$($C_6$-$C_{10}$ aryl), —$(CH_2)_t$(4-10 membered heterocyclic), —C(O)$(CH_2)_t$($C_6$-$C_{10}$ aryl), or —C(O)$(CH_2)_t$ (5-10 membered heterocyclic), where t is an integer from 0 to 5; the alkyl group optionally includes 1 or 2 hetero moieties selected from O, S and —N($R^6$)— with the proviso that two O atoms, two S atoms, or an O and S atom are not attached directly to each other; the aryl and heterocyclic $R^1$ groups are optionally fused to a $C_6$-$C_{10}$ aryl group, a $C_5$-$C_8$ saturated cyclic group, or a 5-10 membered heterocyclic group; 1 or 2 carbon atoms in the foregoing heterocyclic moieties are optionally substituted by an oxo (=O) moiety or an anion of oxygen; the —$(CH_2)_t$— moieties of the foregoing $R^1$ groups optionally include a carbon-carbon double or triple bond where t is an integer from 2 to 5; and the foregoing $R^1$ groups, except H, are optionally substituted by 1 to 3 $R^4$ groups; $R^2$ is H; $R^3$ is —$(CH_2)_t$($C_6$-$C_{10}$ aryl), where t is an integer from 0 to 5; optionally fused to a $C_6$-$C_{10}$ aryl group, a $C_5$-$C_8$ saturated cyclic group, or a 5-10 membered heterocyclic group; the —$(CH_2)_t$— moieties optionally include a carbon-carbon double or triple bond where t is an integer from 2 to 5, and are optionally substituted by 1 to 5 $R^4$ groups; each $R^4$ is independently selected from $C_1$-$C_{10}$ alkyl, $C_2$-$C_{10}$ alkenyl, $C_2$-$C_{10}$ alkynyl, halo, cyano, nitro, trifluoromethyl, trifluoromethoxy, azido, —$OR^5$, —C(O)$R^5$, —C(O)$OR^5$, —$NR^6$C(O)$OR^5$, —OC(O)$R^5$, —$NR^6SO_2R^5$, —$SO_2NR^5R^6$, —$NR^6$C(O)$R^5$, —C(O)$NR^5R^6$, —$NR^5R^6$, —S(O)$_jR^7$ where j is an integer ranging from 0 to 2, —$SO_3H$, —$NR^5(CR^6R^7)_tOR^6$, —$(CH_2)_t$($C_6$-$C_{10}$ aryl), —$SO_2(CH_2)_t$($C_6$-$C_{10}$ aryl), —$S(CH_2)_t$($C_6$-$C_{10}$ aryl), —$O(CH_2)_t$($C_6$-$C_{10}$ aryl), —$(CH_2)_t$ (5-10 membered heterocyclic), and —$(CR^6R^7)_mOR^6$, where m is an integer from 1 to 5 and t is an integer from 0 to 5; the alkyl group optionally contains 1 or 2 hetero moieties selected from O, S and —N($R^6$)— with the proviso that two O atoms, two S atoms, or an O and S atom are not attached directly to each other; the aryl and heterocyclic $R^4$ groups are optionally fused to a $C_6$-$C_{10}$ aryl group, a $C_5$-$C_8$ saturated cyclic group, or a 5-10 membered heterocyclic group; 1 or 2 carbon atoms in the foregoing heterocyclic moieties are optionally substituted by an oxo (=O) moiety or an anion of oxygen; and the alkyl, aryl and heterocyclic moieties of the foregoing $R^4$ groups are optionally substituted by 1 to 3 substituents independently selected from halo, cyano, nitro, trifluoromethyl, trifluoromethoxy, azido, —$NR^6SO_2R^5$, —$SO_2NR^5R^6$, —C(O)$R^5$, —C(O)$OR^5$, —OC(O)$R^5$, —$NR^6$C(O)$R^5$, —C(O)$NR^5R^6$, —$NR^5R^6$, —$(CR^6R^7)_mOR^6$ where m is an integer from 1 to 5, —$OR^5$ and the substituents listed in the definition of $R^5$; and each $R^5$, $R^6$, and $R^7$ is independently H or $C_1$-$C_6$ alkyl.

In a further embodiment of the current invention, $R^3$ in Formula I is —$(CH_2)_t$($C_6$-$C_{10}$ aryl) where t is an integer from 1 to 3 and the $R^3$ group is optionally substituted by 1 to 4 $R^4$ groups.

In another embodiment, $R^3$ in Formula I of the current invention is a benzyl, optionally substituted by 1 to 4 substituents independently selected from halo and $C_1$-$C_4$ alkyl. $R^3$ in Formula I of the current invention is a benzyl substituted by 1 to 4 substituents independently selected from methyl, fluoro, chloro and bromo.

In some embodiments, $R^1$ in Formula I of the current invention is —$(CH_2)_t$ (5-10 membered heterocyclic), where t is an integer from 0 to 5, optionally substituted by 1 or 2 substituents independently selected from $C_1$-$C_4$ alkyl, hydroxy and hydroxymethyl.

The present disclosure provides heterocyclic moiety of the $R^1$ group in Formula I chosen from morpholino, pyrrolidinyl, imidazolyl, piperazinyl, piperidinyl, and 2,5-diazabicyclo[2.2.1]hept-2-yl, the t variable of the $R^1$ group ranges from 2 to 5, and the $R^1$ group is optionally substituted by one or more hydroxy groups.

For example, the heterocyclic moiety of the $R^1$ group in Formula I of the current invention is pyrrolidine.

In further embodiments of the current invention, the active agent is:

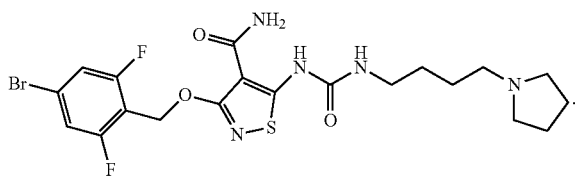

(II)

In some embodiments of the current invention, the active agent is a hydrochloride salt of compound of formula II, namely Compound-I:

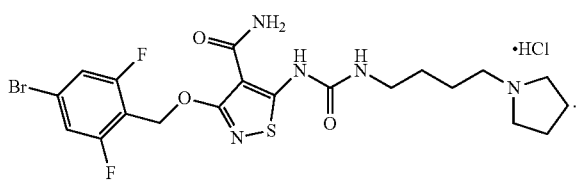

(Compound-I)

The embodiments of the current invention provide formulations of about 0.005% to about 5.0% w/v of the active agent of Formulae (I), (II), or a pharmaceutically acceptable salt thereof for example, Compound-I. In some embodiments, the concentration of Compound-I or its free base (formula II) in the formulations is about 0.005%-about 0.01%, about 0.01%-about 0.05%, about 0.05%-about 0.1%, about 0.1%-about 0.2%, about 0.2%-about 0.3%, about 0.3%-about 0.4%, about 0.4%-about 0.5%, about 0.5%-about 0.6%, about 0.6%-about 0.7%, about 0.7%-about 0.8%, about 0.8%-about 0.9%, about 0.9%-about 1.0%, about 1.1-about 2.0%, about 2.1-about 3.0%, about 3.1-about 4.0%, or about 4.1-about 5.0% w/v for topical administration. In some embodiments the formulations include about 0.005%, about 0.05%, about 0.1%, about 0.2%, about 0.3%, about 0.4%, about 0.5%, about 0.6%, about 0.7%, about 0.8%, about 0.9%, about 1.0%, about 2.0%, about 3.0%, about 4.0%, or about 5.0% w/v of Compound-I or its free base (formula II).

The present disclosure provides a solution of the active agent (e.g., Compound-I), which includes one or more solubilizing agents.

The formulation comprising about 0.005%, about 0.05%, about 0.1%, about 0.2%, about 0.3%, about 0.4%, about 0.5%, about 0.6%, about 0.7%, about 0.8%, about 0.9%, about 1.0%, about 2.0%, about 3.0%, about 4.0%, or about 5.0% w/v of Formulae (I), (II), or a pharmaceutically acceptable salt thereof, for example, Compound-I, includes a solubilizing agent. The solubilizing agent in the formulation may be cyclodextrin, for example, 2-hydroxypropyl-β-cyclodextrin, methyl-β-cyclodextrin, randomly methylated-β-cyclodextrin, ethylated-β-cyclodextrin, triacetyl-β-cyclodextrin, peracetylated-β-cyclodextrin, carboxymethyl-β-cyclodextrin, hydroxyethyl-β-cyclodextrin, 2-hydroxy-3-(trimethylammonio)propyl-β-cyclodextrin, glucosyl-β-cyclodextrin, maltosyl-β-cyclodextrin, sulfobutyl ether-β-cyclodextrin, branched-β-cyclodextrin, hydroxypropyl-γ-cyclodextrin, randomly methylated-γ-cyclodextrin, trimethyl-γ-cyclodextrin, or combinations thereof.

In one embodiment, the solubilizing agent in the formulation is 2-hydroxypropyl-β-cyclodextrin or β-cyclodextrin sulfobutyl ether. The formulation comprises one or more of benzalkonium chloride (BAK), sodium chloride, and a pH adjusting agent.

In additional embodiments, the formulation comprising about 0.005%, about 0.05%, about 0.1%, about 0.2%, about 0.3%, about 0.4%, about 0.5%, about 0.6%, about 0.7%, about 0.8%, about 0.9%, about 1.0%, about 2.0%, about 3.0%, about 4.0%, or about 5.0% w/v of the active agent or a pharmaceutically acceptable salt thereof, includes a buffer, for example, tromethamine. In one embodiment, the formulation comprising about 0.005%, about 0.05%, about 0.1%, about 0.2%, about 0.3%, about 0.4%, about 0.5%, about 0.6%, about 0.7%, about 0.8%, about 0.9%, about 1.0%, about 2.0%, about 3.0%, about 4.0%, or about 5.0% w/v of the active agent or a pharmaceutically acceptable salt thereof, includes about 0.3%-about 1.0% w/v tromethamine, and optionally further includes about 0.005% w/v benzalkonium chloride (BAK).

The present disclosure provides a formulation having a pH value of about 4.5 to about 7.5 at or under about 40° C. In some embodiments, the pH value of the formulation is between about pH 5.0 to about 7.0. In one embodiment the pH value of the formulation is about 6.0 at or under about 40° C.

The current embodiments provide use of a formulation of Compound-I or its free base (formula II) for the manufacture of a medicament for accessing posterior segment of the eye and/or for treating and/or ameliorating a posterior segment disease vasculopathic or inflammatory disease of the eye. These include for example, diabetic retinopathy (including background diabetic retinopathy, proliferative diabetic retinopathy and diabetic macular edema); age-related macular degeneration (AMD) (including neovascular (wet/exudative) AMD, dry AMD, and Geographic Atrophy); pathologic choroidal neovascularization (CNV) from any mechanism (i.e. high myopia, trauma, sickle cell disease; ocular histoplasmosis, angioid streaks, traumatic choroidal rupture, drusen of the optic nerve, and some retinal dystrophies); pathologic retinal neovascularization from any mechanism (i.e., sickle cell retinopathy, Eales disease, ocular ischemic syndrome, carotid cavernous fistula, familial exudative vitreoretinopathy, hyperviscosity syndrome, idiopathic occlusive arteriolitis; birdshot retinochoroidopathy, retinal vasculitis, sarcoidosis and toxoplasmosis); uveitis; retinal vein occlusion (central or branch); ocular trauma; surgery induced edema; surgery induced neovascularization; cystoid macular edema; ocular ischemia; retinopathy of prematurity; Coat's disease; sickle cell retinopathy and/or neovascular glaucoma.

In some embodiments, the exposure time of Compound-I is between 1 and 90 days. In some embodiments, the dosage regimen involves several courses of topical ocular administration of a formulation comprising Compound-I to a subject for between 1 and 90 days. For example, the dosage regimen involves once daily, twice daily, three times daily or four times daily administration of the formulation for between 1 and 90 days. For example, the dosage regimen involves once, twice, three times, or four times administration of the formulation on alternate days (i.e., on day 1, 3, 5, 7 etc.) for up to 90 days. For example, the dosage regimen involves administering once on day 1, once or twice on day 2-day 90. For example, the dosage regimen involves administering once, twice, three times, or four times on day 1, followed by once daily for 2-90 days. For example, the dosage regimen involves administering once, twice, three times, four times on day 1, followed by once, twice, three times, or four times on alternate days (i.e., on day 1, 3, 5, 7 etc.) for up to 90 days. For example, one dosage regimen involves once per day or twice per day for 1, 2, 3, 4, or 5 consecutive days. For twice or three daily dosage regimen, subjects receive topical ocular dose of a Compound-I formulation on days 1 and 4 approximately about 4, 6, or 8 hours apart. In another embodiment, subjects receive topical ocular doses of a Compound-I formulation approximately about 4, 6, or 8 hours apart for four consecutive days. In some embodiments, subjects receive one or two doses of topical ocular dose of Compound-I formulation per day for 5 consecutive days. In yet other embodiments, subjects receive one or two doses of topical ocular dose of Compound-I formulation for 5-90 consecutive days. In some embodiments, subjects receive one or two doses of topical ocular dose of Compound-I formulation for at least 25 consecutive days. In one embodiment, subjects receive one or two topical ocular doses for at least 90 consecutive days or more.

For example, a formulation comprising about 2 mg/mL BID of Compound-I is administered to one eye or both eyes of a subject for between 1 and 90 days. In some embodiments a formulation comprising about 3 mg/mL BID of Compound-I is administered to one eye or both eyes of a subject for between 1 and 90 days. In some embodiments a formulation comprising about 3 mg/mL QD of Compound-I is administered to one eye or both eyes of a subject for between 1 and 90 days. In some embodiments a formulation comprising about 4 mg/mL BID of Compound-I is administered to one eye or both eyes of a subject for between 1 and 90 days. In some embodiments a formulation comprising about 4 mg/mL QD of Compound-I is administered to one eye or both eyes of a subject for between 1 and 90 days. In some embodiments a formulation comprising about 5 mg/mL BID of Compound-I is administered to one eye or both eyes of a subject for between 1 and 90 days. In some embodiments a formulation comprising about 5 mg/mL QD of Compound-I is administered to one eye or both eyes of a subject for between 1 and 90 days. In some embodiments a formulation comprising about 6 mg/mL BID of Compound-I is administered to one eye or both eyes of a subject for between 1 and 90 days. In some embodiments a formulation comprising about 6 mg/mL QD of Compound-I is administered to one eye or both eyes of a subject for between 1 and 90 days. The dosage regimen for between 1 and 90 days may be any of the regimens involving consecutive or alternate days described in the paragraph above.

In some embodiments, the formulation of Formula (II) or Compound-I is administered to one eye or both eyes of a subject. For example, about 0.2%-about 0.6% (w/v) of the compound of Formula (II) or about 0.1%-0.7% (w/v) of Compound-I comprising formulation of the current disclosure is administered once a day (QD) or twice a day (BID) to one eye or both eyes of a subject for between 1 and 90 days. In some embodiments, Formula (II) compound or Compound-I is complexed with a complexing agent, e.g., cyclodextrin (e.g., hydroxypropyl-β-cyclodextrin (HP-β-CD, KLEPTOSE® HPB) (%)) in ratio of about 1:8, in which about 2%-13% (w/v) cyclodextrin (e.g., KLEPTOSE® HPB (%)) is added to the formulation. The formulation further comprises about 0.1%-about 0.2% buffer, e.g., 10 mM phosphate buffer. The desired osmolality of the formulation is about 200-about 300 mOsm, achieved by adding quantity sufficient to achieve the osmolality with a salt, e.g., sodium chloride. The pH of the formulation is about 6.0.

DETAILED DESCRIPTION OF THE INVENTION

The materials, compounds, compositions, articles, and methods described herein may be understood more readily by reference to the following detailed description of specific aspects of the disclosed subject matter and the Examples included therein. Before the present materials, compounds, compositions, articles, devices, and methods are disclosed and described, it is to be understood that the aspects described below are not limited to specific synthetic methods or specific reagents, as such may vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

The present invention provides compositions or formulations that contain an active agent for use in the treatment of ocular disorders caused by endothelial cell proliferation, enhanced vascular permeability, inflammation, or angiogenesis. The formulations of the invention are useful in preventing or inhibiting neovascularization and vascular leakage associated with such ocular disorders. In some cases, the formulations of the invention cause regression of neovascularization. Briefly, within the context of the present invention, active agents should be understood to be any molecule, either synthetic or naturally occurring, which acts to inhibit vascular growth, reduce vascular permeability, and/or decrease inflammation. In particular, the present invention provides formulations comprising an active agent in a therapeutically effective amount.

General Definitions

In this specification and in the claims that follow, reference is made to a number of terms, which shall be defined to have the following meanings: All percentages, ratios and proportions herein are by weight, unless otherwise specified. All temperatures are in degrees Celsius (° C.) unless otherwise specified.

By "pharmaceutically acceptable" is meant a material that is not biologically or otherwise undesirable, i.e., the material can be administered to an individual along with the relevant active compound without causing clinically unacceptable biological effects or interacting in a deleterious manner with any of the other components of the pharmaceutical composition or formulation in which it is contained.

A weight percent of a component, unless specifically stated to the contrary, is based on the total weight of the formulation or composition in which the component is included.

By "effective amount" as used herein means "an amount of one or more of the disclosed compounds, effective at dosages and for periods of time necessary to achieve the desired or therapeutic result." An effective amount may vary according to factors known in the art, such as the disease state, age, sex, and weight of the human or animal being treated. Although particular dosage regimes may be described in examples herein, a person skilled in the art would appreciate that the dosage regime may be altered to provide optimum therapeutic response. For example, several divided doses may be administered daily or the dose may be proportionally reduced as indicated by the exigencies of the therapeutic situation. In addition, the formulations of this disclosure can be administered as frequently as necessary to achieve a therapeutic amount.

"Excipient" is used herein to include any other compound that may be contained in or combined with one or more of the disclosed inhibitors that is not a therapeutically or biologically active compound. As such, an excipient should be pharmaceutically or biologically acceptable or relevant (for example, an excipient should generally be non-toxic to the subject). "Excipient" includes a single such compound and is also intended to include a plurality of excipients. For the purposes of the present disclosure the term "excipient" and "carrier" are used interchangeably throughout the description of the present disclosure and said terms are defined herein as, "ingredients which are used in the practice of formulating a safe and effective pharmaceutical composition."

As used herein, by a "subject" is meant an individual. Thus, the "subject" can include domesticated animals (e.g., cats, dogs, etc.), livestock (e.g., cattle, horses, pigs, sheep, goats, etc.), laboratory animals (e.g., mouse, rabbit, rat, guinea pig, etc.), and birds. "Subject" can also include a primate or a human.

By "reduce" or other forms of the word, such as "reducing" or "reduction," is meant lowering of an event or characteristic (e.g., vascular leakage, or tissue swelling). It is understood that this is typically in relation to some standard or expected value, in other words it is relative, but that it is not always necessary for the standard or relative value to be referred to.

The term "treat" or other forms of the word such as "treated" or "treatment" is used herein to mean that administration of a compound of the present invention mitigates a disease or a disorder in a host and/or reduces, inhibits, or eliminates a particular characteristic or event associated with a disorder (e.g., vascular leakage).

Insofar as the methods of the present invention are directed to preventing disorders, it is understood that the term "prevent" does not require that the disease state be completely thwarted. Rather, as used herein, the term preventing refers to the ability of the skilled artisan to identify a population that is susceptible to disorders, such that administration of the compounds of the present invention may occur prior to onset of a disease. The term does not imply that the disease state be completely avoided.

The term "ameliorating" or other forms of the word such as "ameliorate" is used herein to mean that administration of a therapeutic agent of the present invention mitigates one or more symptoms of a disease or a disorder in a host and/or reduces, inhibits, or eliminates a particular symptom associated with the disease or disorder prior to and/or post administration of the therapeutic agent.

The disclosed compounds affect vascular leakage or pathological neovascularization by inhibiting a receptor tyrosine kinase.

Throughout the description and claims of this specification the word "comprise" and other forms of the word, such as "comprising" and "comprises," means including but not limited to, and is not intended to exclude, for example, other additives, or components.

As used in the description and the appended claims, the singular forms "a," "an," and "the" include plural referents unless the context clearly dictates otherwise.

"Optional" or "optionally" means that the subsequently described event or circumstance can or cannot occur, and that the description includes instances where the event or circumstance occurs and instances where it does not.

The term "about" refers to any minimal alteration in the concentration or amount of a therapeutic agent that does not change the efficacy of the agent in preparation of a formulation and in treatment of a disease or disorder. For example, without being limiting, the concentration of a therapeutic agent would be effective if the concentration is varied between 0.005% to 5.0% (±0.0005%). The term "about" with respect to concentration range of the therapeutic/active agents of the current invention also refers to any variation of a stated amount or range which would be an effective amount or range.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it is understood that the particular value forms another aspect. It is further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed, then "less than or equal to" the value, "greater than or equal to the value," and possible ranges between values are also disclosed, as appropriately understood by the skilled artisan. For example, if the value "10" is disclosed, then "less than or equal to 10" as well as "greater than or equal to 10" is also disclosed. It is also understood that throughout the application data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

The term "halo", as used herein, unless otherwise indicated, includes fluoro, chloro, bromo or iodo. Preferred halo groups are fluoro, chloro and bromo.

The term "alkyl," as used herein, unless otherwise indicated, includes both branched and straight-chain saturated aliphatic hydrocarbon groups having the specified number of carbon atoms. For example, C1-6 alkyl is intended to include C1, C2, C3, C4, C5, and C6 alkyl groups. Examples of alkyl include, but are not limited to, methyl, ethyl, n-propyl, i-propyl, n-butyl, s-butyl, t-butyl, n-pentyl, s-pentyl, and n-hexyl. In certain embodiments, a straight chain or branched chain alkyl has six or fewer carbon atoms in its backbone (e.g., $C_1$-$C_6$ for straight chain, $C_3$-$C_6$ for branched chain), and in another embodiment, a straight chain or branched chain alkyl has four or fewer carbon atoms. Likewise, cycloalkyls have from three to eight carbon atoms in their ring structure, and in other embodiments, cycloalkyls have five or six carbons in the ring structure. Alkyl can be substituted by replacing hydrogen on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "aralkyl" moiety is an alkyl substituted with an aryl (e.g., phenylmethyl (benzyl)).

The term "alkenyl," as used herein, unless otherwise indicated, includes unsaturated aliphatic groups analogous in length and possible substitution to the alkyls described above, but that contain at least one double bond. For example, the term "alkenyl" includes straight-chain alkenyl groups (e.g., ethenyl, propenyl, butenyl, pentenyl, hexenyl, heptenyl, octenyl, nonenyl, decenyl), branched-chain alkenyl groups, cycloalkenyl (e.g., alicyclic) groups (e.g., cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. In certain embodiments, a straight chain or branched chain alkenyl group has six or fewer carbon atoms in its backbone (e.g., $C_2$-$C_6$ for straight chain, $C_3$-$C_6$ for branched chain). Likewise, cycloalkenyl groups may have from three to eight carbon atoms in their ring structure, and in some embodiments, cycloalkenyl groups have five or six carbons in the ring structure. The term "$C_2$-$C_6$" includes alkenyl groups containing two to six carbon atoms. The term "$C_3$-$C_6$" includes alkenyl groups containing three to six carbon atoms. Alkenyl can be substituted by replacing hydrogen on one or more hydrocarbon backbone carbon atoms. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkynyl", as used herein, unless otherwise indicated, includes unsaturated aliphatic groups analogous in length and possible substitution to the alkyls described above, but which contain at least one triple bond. For example, "alkynyl" includes straight-chain alkynyl groups (e.g., ethynyl, propynyl, butynyl, pentynyl, hexynyl, heptynyl, octynyl, nonynyl, decynyl), branched-chain alkynyl groups, and cycloalkyl or cycloalkenyl substituted alkynyl groups. In certain embodiments, a straight chain or branched chain alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms. The term "$C_3$-$C_6$" includes alkynyl groups containing three to six carbon atoms. Alkynyl can be substituted by replacing hydrogen on one or more hydrocarbon backbone carbon atoms. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkoxy," as used herein, unless otherwise indicated, includes O-alkyl groups wherein "alkyl" is as defined above.

The term "aryl," as used herein, unless otherwise indicated, includes 5- and 6-membered "unconjugated", or single-ring, aromatic groups that may include from zero to four heteroatoms, as well as "conjugated", or multicyclic, systems with at least one aromatic ring. Examples of aryl groups include benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, naphthyridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, methylenedioxyphenyl).

The term "4-10 membered heterocyclic," as used herein, unless otherwise indicated, includes aromatic and non-aromatic heterocyclic groups containing one or more heteroatoms each selected from O, S and N, wherein each heterocyclic group has from 4-10 atoms in its ring system. Non-aromatic heterocyclic groups include groups having only 4 atoms in their ring system, but aromatic heterocyclic groups must have at least 5 atoms in their ring system. An example of a 4 membered heterocyclic group is azetidinyl (derived from azetidine). An example of a 5 membered heterocyclic group is thiazolyl and an example of a 10 membered heterocyclic group is quinolinyl. Examples of non-aromatic heterocyclic groups are pyrrolidinyl, tetrahydrofuranyl, tetrahydrothienyl, tetrahydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo [4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the compounds listed above, may be C-attached or N-attached where such is possible. For instance, a group derived from pyrrole may be pyrrol-1-yl (N-attached) or pyrrol-3-yl (C-attached). The "4-10 membered heterocyclic" moiety can be substituted.

The phrase "pharmaceutically acceptable salt(s)," as used herein, unless otherwise indicated, includes salts of acidic or basic groups which may be present in the compounds of Formula (I) or (II). The compounds of Formula (I) or (II) that are basic in nature are capable of forming a wide variety of salts with various inorganic and organic acids. The acids that may be used to prepare pharmaceutically acceptable acid addition salts of such basic compounds of Formula (I) or (II) are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts.

Those compounds of Formula (I) that are acidic in nature are capable of forming base salts with various pharmacologically acceptable cations. Examples of such salts include the alkali metal or alkaline earth metal salts and particularly, the sodium and potassium salts. In some embodiments, the salt is an acid addition salt, e.g. HCl salt.

Certain compounds of Formula (I) may have asymmetric centers and therefore exist in different enantiomeric forms. This invention relates to the use of all optical isomers and stereoisomers of the compounds of Formula (I) and mixtures thereof. The compounds of Formula (I) may also exist as E/Z geometric isomers or tautomers. This invention relates to the use of all such geometric isomers and tautomers and mixtures thereof.

The subject invention also includes isotopically-labeled compounds, and the pharmaceutically acceptable salts thereof, which are identical to those recited in Formula (I), but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{35}S$, $^{18}F$, and $^{36}Cl$, respectively. Compounds of the present invention, conjugates thereof, and pharmaceutically acceptable salts of said compounds or of said conjugates which contain the aforementioned isotopes and/or other isotopes of other atoms are within the scope of this invention. Certain isotopically-labeled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$ isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds of Formulae (I) of this invention and esters or lipid conjugates thereof can generally be prepared by carrying out the procedures disclosed in the Schemes and/or in the Examples and Preparations below, by substituting a readily available isotopically labeled reagent for a non-isotopically labeled reagent.

This invention also encompasses pharmaceutical formulations containing derivatives of compounds of the Formula (I) or pharmaceutically acceptable salts thereof. Compounds of Formula (I), or pharmaceutically acceptable salts thereof, having free amino, or amido groups can be converted into conjugated derivatives, wherein an amino acid residue, or a polypeptide chain of two or more (e.g., two, three or four) amino acid residues is covalently joined through an amide or ester bond to a free amino group of compounds of Formula (I), or pharmaceutically acceptable salts thereof. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of derivatives are also encompassed. Amide and ester moieties may incorporate groups including but not limited to ether, amine and carboxylic acid functionalities. Free hydroxy groups may be derivatized using groups including but not limited to hemisuccinates, phosphate esters, dimethylaminoacetates, and phosphoryloxymethyloxycarbonyls, as outlined in D. Fleisher, et al., ADVANCED DRUG DELIVERY REVIEWS (1996) 19, 115. Carbamate conjugates of hydroxy and amino groups are also included, as are carbonate conjugates and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Derivatives of this type are described in R. P. Robinson et al., J. MEDICINAL CHEMISTRY (1996) 39, 10.

The term "kinase" refers to any enzyme that catalyzes the addition of phosphate groups to a protein residue, for example, serine and threonine kinases catalyze the addition of phosphate groups to serine and threonine residues.

The terms "VEGFR kinase," "VEGFR," refer to any of the vascular endothelial growth factor receptors.

The terms "VEGF signaling," and "VEGF cascade" refer to both the upstream and downstream components of the VEGF signaling cascade.

The term "pharmaceutically acceptable" refers to the fact that the carrier, diluent or excipient must be compatible with the other ingredients of the formulation and not deleterious to the recipient thereof.

The terms "administration of a compound" or "administering a compound" refer to the act of providing a compound of the invention or pharmaceutical formulation to the subject in need of treatment.

The term "vasculostasis" refers to the maintenance of the homeostatic vascular functioning leading to the normal physiologic functioning.

The term "vasculostatic agents" refers to agents that seek to address conditions in which vasculostasis is compromised by preventing the loss of or restoring or maintaining vasculostasis.

In the current disclosure "composition" and "formulation" are used interchangeably and refer to the conventional understanding, as known in the art, of a composition or formulation.

The current invention relates to an ophthalmic formulation. In some embodiments, the ophthalmic formulation of the current invention is a gel formulation or a semi-gel formulation, or both.

"Gel" according to the current invention is a semi-solid dosage form of the current invention, containing suspended particles. A semisolid is not pourable; it does not flow or conform to its container at room temperature. A semisolid does not flow at low shear stress and generally exhibits plastic flow behavior. A colloidal dispersion is a system in which particles of colloidal dimension (i.e., typically between 1 nm and 1 μm) are distributed uniformly throughout a liquid.

In some embodiments, "gel" is a semisolid system consisting either of suspensions of small inorganic particles or of organic molecules interpenetrated by a liquid. "Gels" are classed either as single-phase or two-phase systems. "Gels" also consist of a mesophase, or state of matter intermediate between a liquid and a solid that represents a partially ordered structure, which is the state for the active agents in the "Gel Drop" of the current embodiments. A two-phase gel consists of a network of small discrete particles. In a two-phase system, the gel mass sometimes is referred to as magma (e.g., Bentonite Magma) if the particle size of the suspended material is large. Both gels and magmas are thixotropic, forming semisolids on standing and becoming liquid on agitation. The semisolid formulations should be shaken before administration to ensure homogeneity and should be so labeled (see Suspensions). Single-phase gels consist of organic macromolecules uniformly distributed throughout a liquid in such a manner that no apparent boundaries exist between the dispersed macromolecules and the liquid. Single phase gels may also consist of organic low molecular weight (LMW) molecules where the component responsible for gelation is the actual active ingredient. These so called "LMW hydrogels" are different from traditional gelators of water such as high molecular weight synthetic polymers, polysaccharides, and proteins. High molecular weight gelators are highly ordered and uni-directional due to hydrogen bonding whereas the forces governing LMW hydrogels are largely non-directional van der Waals forces (hydrophobic) interactions. In practice LMW hydrogels are observed as highly anisotropic (typically fibrillar) structures that propagate throughout the liquid yielding a physically branched or entangled network. The gels can thus be non-ordered to slightly ordered showing some birefringence, liquid crystal character. Gels are administered topically or, after shaking, in the form of a hydrogel as an eye drop.

The semisolid "gel" according to the current invention is a semisolid per USP definitions and literature referenced therein. The semisolid formulation apparent viscosity increases with concentration. The clinical dosage strength of the current formulation ranges from a low strength of ≤1 mg/mL (0.1%) to a high strength of ≤6 mg/mL (0.6%). Low strength doses are least viscous and fall under the category of a "solution," whereas higher strengths are more viscous and fit the definition of a gel.

"Jelly" according to the current invention is a class of gels, which are semisolid systems that consist of suspensions made up either small inorganic particles or large organic molecules interpenetrated by a liquid, in which the structural coherent matrix contains a high portion of liquid, usually water.

"Solution" according to the current invention is a clear, homogeneous liquid dosage form that contains one or more chemical substances dissolved in a solvent or mixture of mutually miscible solvents. A solution is a liquid preparation that contains one or more dissolved chemical substances in a suitable solvent or mixture of mutually miscible solvents. Because molecules of a drug substance in solution are uniformly dispersed, the use of solutions as dosage forms generally provides assurance of uniform dosage upon administration and good accuracy when the solution is diluted or otherwise mixed.

"Liquid" according to the current invention is a dosage form consisting of a pure chemical in its liquid state. A liquid is pourable; it flows and conforms to its container at room temperature. Liquids display Newtonian or pseudoplastic flow behavior.

"Suspension" according to the current invention is a liquid dosage form that contains solid particles dispersed in a liquid vehicle.

The compounds of the invention are formulated into therapeutic formulations as natural or salt forms. Pharmaceutically acceptable non-toxic salts include the base addition salts (formed with free carboxyl or other anionic groups) which are derived from inorganic bases such as, for example, sodium, potassium, ammonium, calcium, or ferric hydroxides, and such organic bases as isopropylamine, trimethylamine, 2-ethylamino-ethanol, histidine, procaine, and the like. Such salts are formed as acid addition salts with any free cationic groups and generally are formed with inorganic acids such as, for example, hydrochloric, sulfuric, or phosphoric acids, or organic acids such as acetic, citric, p-toluenesulfonic, methanesulfonic acid, oxalic, tartaric, mandelic, and the like. Salts of the invention include amine salts formed by the protonation of an amino group with inorganic acids such as hydrochloric acid, hydrobromic acid, hydroiodic acid, sulfuric acid, phosphoric acid, and the like. Salts of the invention also include amine salts formed by the protonation of an amino group with suitable organic acids, such as p-toluenesulfonic acid, acetic acid, and the like. Additional excipients which are contemplated for use in the practice of the present invention are those available to those of ordinary skill in the art, for example, those found in the United States Pharmacopoeia Vol. XXII and National Formulary Vol. XVII, U.S. Pharmacopoeia Convention, Inc., Rockville, Md. (1989), the relevant contents of which is incorporated herein by reference. In addition, polymorphs of the invention compounds are included in the present invention.

The embodiments of the current invention provide an ophthalmic composition or formulation for treating ocular neovascularization with an active agent of Formula I:

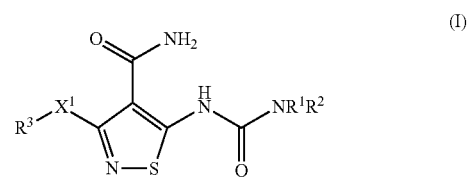

(I)

or a pharmaceutically acceptable salt thereof; and pharmaceutically acceptable excipients; the active agent or the pharmaceutically acceptable salt is present in about 0.02% to about 1.0% w/v, and where the active agent is identified as: $X^1$ is O or S; $R^1$ is H, $C_1$-$C_{10}$ alkyl, $C_2$-$C_{10}$ alkenyl, $C_2$-$C_{10}$ alkynyl, —C(O)($C_1$-$C_{10}$ alkyl), —$(CH_2)_t$($C_6$-$C_{10}$ aryl), —$(CH_2)_t$(4-10 membered heterocyclic), —C(O) $(CH_2)_t$ ($C_6$-$C_{10}$ aryl), or —C(O)$(CH_2)_t$ (5-10 membered heterocyclic), where t is an integer from 0 to 5; the alkyl group optionally includes 1 or 2 hetero moieties selected from O, S and —N($R^6$)— with the proviso that two O atoms, two S atoms, or an O and S atom are not attached directly to each other; the aryl and heterocyclic $R^1$ groups are optionally fused to a $C_6$-$C_{10}$ to aryl group, a $C_5$-$C_8$ saturated cyclic group, or a 5-10 membered heterocyclic group; 1 or 2 carbon atoms in the foregoing heterocyclic moieties are optionally substituted by an oxo (=O) moiety or an anion of oxygen; the —$(CH_2)_t$— moieties of the foregoing $R^1$ groups optionally include a carbon-carbon double or triple bond where t is an integer from 2 to 5; and the foregoing $R^1$ groups, except H, are optionally substituted by 1 to 3 $R^4$ groups; $R^2$ is H; $R^3$ is —$(CH_2)_t$($C_6$-$C_{10}$ aryl), where t is an integer from 0 to 5; optionally fused to a $C_6$-$C_{10}$ aryl group, a $C_5$-$C_8$ saturated cyclic group, or a 5-10 membered heterocyclic group; the —$(CH_2)_t$— moieties optionally include a carbon-carbon double or triple bond where t is an integer from 2 to 5, and are optionally substituted by 1 to 5 $R^4$ groups; each $R^4$ is independently selected from $C_1$-$C_{10}$ alkyl, $C_2$-$C_{10}$ alkenyl, $C_2$-$C_{10}$ alkynyl, halo, cyano, nitro, trifluoromethyl, trifluoromethoxy, azido, —$OR^5$, —C(O)$R^5$, —C(O)$OR^5$, —$NR^6$C(O)$OR^5$, —OC(O)$R^5$, —$NR^6SO_2R^5$, —$SO_2NR^5R^6$, —$NR^6$C(O)$R^5$, —C(O)$NR^5R^6$, —$NR^5R^6$, —S(O)$_jR^7$ where j is an integer ranging from 0 to 2, —$SO_3H$, —$NR^5$ $(CR^6R^7)_tOR^6$, —$(CH_2)_t$($C_6$-$C_{10}$ aryl), —$SO_2(CH_2)_t$($C_6$-$C_{10}$ aryl), —S$(CH_2)_t$($C_6$-$C_{10}$ aryl), —O$(CH_2)_t$($C_6$-$C_{10}$ aryl), —$(CH_2)_t$ (5- 10 membered heterocyclic), and —$(CR^6R^7)_mOR^6$, where m is an integer from 1 to 5 and t is an integer from 0 to 5; the alkyl group optionally contains 1 or 2 hetero moieties selected from O, S and —N($R^6$)— with the proviso that two O atoms, two S atoms, or an O and S atom are not attached directly to each other; the aryl and heterocyclic $R^4$ groups are optionally fused to a $C_6$-$C_{10}$ aryl group, a $C_5$-$C_8$ saturated cyclic group, or a 5-10 membered heterocyclic group; 1 or 2 carbon atoms in the foregoing heterocyclic moieties are optionally substituted by an oxo (=O) moiety or an anion of oxygen; and the alkyl, aryl and heterocyclic moieties of the foregoing $R^4$ groups are optionally substituted by 1 to 3 substituents independently selected from halo, cyano, nitro, trifluoromethyl, trifluoromethoxy, azido, —$NR^6SO_2R^5$, —$SO_2NR^5R^6$, —C(O)$R^5$, —C(O)$OR^5$, —OC(O)$R^5$, —$NR^6$C(O)$R^5$, —C(O)$NR^5R^6$, —$NR^5R^6$, —$(CR^6R^7)_mOR^6$ where m is an integer from 1 to 5, —$OR^5$ and the substituents listed in the definition of $R^5$; and each $R^5$, $R^6$, and $R^7$ is independently H or $C_1$-$C_6$ alkyl.

In further embodiment of the current invention, $R^3$ in Formula I of the current invention is —$(CH_2)_t$($C_6$-$C_{10}$ aryl) where t is an integer from 1 to 3 and the $R^3$ group is optionally substituted by 1 to 4 $R^4$ groups.

In another embodiment, $R^3$ in Formula I of the current invention is a benzyl optionally substituted by 1 to 4 substituents independently selected from halo and $C_1$-$C_4$ alkyl. For example, $R^3$ in Formula I of the current invention is a benzyl substituted by 1 to 4 substituents independently selected from methyl, fluoro, chloro and bromo.

$R^1$ in Formula I of the current invention is —$(CH_2)_t$ (5-10 membered heterocyclic), where t is an integer from 0 to 5, optionally substituted by 1 or 2 substituents independently selected from $C_1$-$C_4$ alkyl, hydroxy and hydroxymethyl.

The heterocyclic moiety of the $R^1$ group in Formula I of the current invention is selected from morpholino, pyrrolidinyl, imidazolyl, piperazinyl, piperidinyl, and 2,5-diazabicyclo[2.2.1]hept-2-yl, the t variable of the $R^1$ group ranges from 2 to 5, and the $R^1$ group is optionally substituted by one or more hydroxy groups.

For example, the heterocyclic moiety of the $R^1$ group in Formula I of the current invention is pyrrolidine.

In further embodiments of the current invention, the active agent is:

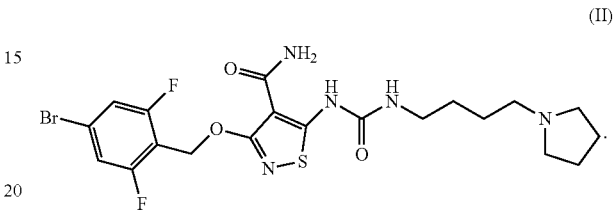

(II)

A compound of the current invention is 3-[(4-bromo-2,6-difluorophenyl)methoxy]-5-[[[[4-(1-pyrrolidinyl)butyl] amino]carbonyl]amino]-4-isothiazolecarboxamide hydrochloride, of molecular formula: $C_{20}H_{24}BrF_2N_5O_3S$·HCl, molecular weight: 568.86 g/mol, and with the property that the molecule does not contain an asymmetric center and is not chiral. A compound of the current invention is represented by Compound-I:

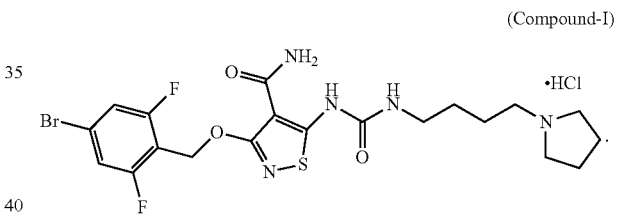

(Compound-I)

The Compound-I of the current invention is an inhibitor of the tyrosine kinase activity of VEGFR-2, which blocks VEGF-stimulated auto-phosphorylation of this receptor as well as endothelial cell proliferation. It is selective (>500×) relative to the concentration required to inhibit the epidermal growth factor receptor (EGFR) and the insulin receptor (IR) tyrosine kinases. Compound-I is described in U.S. Pat. No. 6,235,764.

General Properties

Compound-I of the present invention has the characteristics as shown in Table 1. The embodiments provide three formulations of Compound-I or its free base—the Formula II compound.

TABLE 1A

General Properties of Compound-I Drug Substance

| Property | Result |
|---|---|
| Chemical Name [CAS No] Codes: Compound-I | 3-[(4-bromo-2,6-difluorophenyl)methoxy]-5-[[[[4-(1-pyrrolidinyl)butyl]amino]carbonyl]amino]-4-isothiazolecarboxamide hydrochloride [252003-71-7] |
| Appearance (color, physical form) | White crystalline solid |

TABLE 1A-continued

General Properties of Compound-I Drug Substance

| Property | Result | |
|---|---|---|
| Melting range | 222.2-224.8° C. | |
| pKa (water) | 10.5 | |
| Solubility (mg/mL) | Methanol: | 4.3 |
| | Ethanol: | 0.7 |
| | Acetonitrile: | 0.04 |
| | Tetrahydrofuran: | 0.02 |
| | Hexanes: | <0.01 |
| | 0.1 N NaOH: | 0.05 |
| | pH 9.0 (0.05 m $Na_2HPO_4$): | 0.7 |
| | pH 7.5 (0.05M $NaH_2PO_4$): | 1.0 |
| | 0.1 N HCl: | 0.04 |
| | Deionized water | 0.5-1.2[b] |

The composition of the Compound-I formulations are listed in Table 1B. The formulation materials are listed in Table 1C.

TABLE 1B

Compound-I formulations: Gel Drop, suspension, and solution.

| Formulation Forms | Composition |
|---|---|
| Ophthalmic gel drops | 0.05% Sodium Phosphate, Monobasic, Monohydrate<br>1.0-2.0% Glycerin<br>with or without 0.005% Benzalkonium Chloride, NF (BAK)<br>pH~6.0-7.0 |
| Tris-based suspensions | 0.6% Tromethamine, USP (Tris)<br>1.0-2.0% Glycerin, USP<br>with or without 0.005% Benzalkonium Chloride, NF (BAK)<br>pH~6.0-7.0 |
| Cyclodextrin-based solutions | 1% to 20% hydroxypropyl-β-cyclodextrin (HP-β-CD, KLEPTOSE ® HPB)<br>0.1% to 0.9% sodium chloride<br>pH~6.0-7.0<br>or<br>1% to 20% sulfobutylether-β-cyclodextrin (SBE-β-CD, CAPTISOL ®)<br>with or without 0.122% Tromethamine (Tris)<br>0.1-0.2% sodium phosphate, dibasic, anhydrous<br>0%-0.6% sodium chloride<br>pH~6.0-7.0<br>or<br>1% to 20% HP-β-CD (KLEPTOSE ® HPB or KLEPTOSE ®HP)<br>0.1- 0.2% sodium phosphate, dibasic, anhydrous<br>0.50%-0.6% sodium chloride<br>pH~6.0-7.0 |

TABLE 1C

Formulation materials

| Material | Function |
|---|---|
| Compound-I | Active Drug Substance |
| Sodium Chloride | Tonicity Modifier |
| Sulfobutyl ether-β-cyclodextrin (CAPTISOL ®, SβECD)<br>2-hydroxypropyl-β-cyclodextrin (KLEPTOSE ® HPB Parenteral Grade, HPβCD) | Solubilizing agents |
| Trometamol (Tris)<br>Dibasic phosphate buffer | Buffer |
| 2.0 N NaOH<br>0.1 N HCl | Adjust pH |

Ophthalmic Solutions

The present invention provides formulations of Compound-I and/or its free base (Formula II compound), formed as a solution with viscosity similar to water. The solution includes pharmaceutically acceptable agents/excipients, for example, without being limiting, cyclodextrin. The solution thus formed is clear and colorless solution, suitable for topical administration to the eye.

The solutions of the present invention reduce anterior segment exposure of the active agent; thereby they allow increased concentration of the active agent in the solution and increased frequency of delivery, thus, promoting maintained high concentration of the active agent in the posterior segment of the eye.

The solutions of the invention comprise about 0.005° % to about 5.0% w/v of the active agent of Formulae I, or a pharmaceutically acceptable salt thereof, for example, Compound-I. In some embodiments, the concentration of Compound-I or its free base (formula II) in the solutions is about 0.005%-about 0.01%, about 0.01%-about 0.05%, about 0.05%-about 0.1%, about 0.1%-about 0.2%, about 0.2%-about 0.3%, about 0.3%-about 0.4%, about 0.4%-about 0.5%, about 0.5%-about 0.6%, about 0.6%-about 0.7%, about 0.7%-about 0.8%, about 0.8%-about 0.9%, about 0.9%-about 1.0%, about 1.0-about 2.0%, about 2.0-about 3.0%, about 3.0-about 4.0%, or about 4.0-about 5.0% w/v for topical administration. In some embodiments, the solutions include about 0.005%, about 0.05%, about 0.1%, about 0.2%, about 0.3%, about 0.4%, about 0.5%, about 0.6%, about 0.7%, about 0.8%, about 0.9%, about 1.0%, about 2.0%, about 3.0%, about 4.0%, or about 5.0% w/v of Compound-I or its free base (formula II).

In some embodiments, the formulation comprises cyclodextrin for improving solubility of Compound-I. Cyclodextrin, an oligosaccharide made up of six to eight dextrose units joined through one or four bonds increases solubility of active agents that have poor or low solubility in water or aqueous solutions (e.g., in PBS buffer). Cyclodextrins form hydrophilic complexes with hydrophobic active agents.

One or more cyclodextrins are used in the solution of the present invention. Non-limiting examples of cyclodextrins for use in formulation of the current invention are, for example: 2-hydroxypropyl-β-cyclodextrin, methyl-β-cyclodextrin, randomly methylated-β-cyclodextrin, ethylated-β-cyclodextrin, triacetyl-β-cyclodextrin, peracetylated-β-cyclodextrin, carboxymethyl-β-cyclodextrin, hydroxyethyl-β-cyclodextrin, 2-hydroxy-3-(trimethylammonio)propyl-β-cyclodextrin, glucosyl-β-cyclodextrin, maltosyl-β-cyclodextrin, sulfobutyl ether-β-cyclodextrin, branched-β-cyclodextrin, hydroxypropyl-γ-cyclodextrin, randomly methylated-γ-cyclodextrin, trimethyl-γ-cyclodextrin, or combinations thereof.

In some embodiments, the solution of Formula II compound or Compound-I comprising cyclodextrin is a clear and colorless solution and has a viscosity similar to water. The present disclosure provides a solution comprising Compound-I and one or more cyclodextrin for topical application and is topically applied to the eye.

The ophthalmic solution comprising cyclodextrin of the current invention includes pharmaceutical excipients chosen at or below concentrations optimal for ophthalmic solution. The excipients of the current invention are, for example, benzalkonium chloride (BAK) and NaCl. In some embodiments, the ophthalmic solution comprises about 0.001-about 0.005% w/v Benzalkonium chloride (BAK). The BAK amount varies depending on the need of the invention.

The ophthalmic solution comprises, for example, without being limiting, about 0.005%-5.0% Compound-I or its free base, about 2-about 25% cyclodextrin, e.g., without being limiting, Hydroxypropyl-β-cyclodextrin (HPβCD) or methylcyclodextrin (KLEPTOSE® HPB), and/or sulfobutyl ether-β-cyclodextrin (CAPTISOL®), about 0.1-about 0.7% salt, e.g., without being limiting, NaCl, and/or about 0.005% of an anti-microbial agent, for example, without being limiting, Benzalkonium chloride (BAK). The formulation comprises Compound-I or its free base to cyclodextrin ratio 1:2, 1:3, 1:4, 1:5, 1:6, 1:7, 1:8, 1:9, 1:10, or between 1:10 and 1:20. In some embodiments, the ophthalmic solution comprising cyclodextrin further comprises tromethamine (also known as Tris, Tris(Hydroxymethyl)aminomethane, or Tris buffer). In some embodiments, the ophthalmic solution comprises about 1% Tris.

Ophthalmic solutions of the current embodiments include, for example, without being limiting: about 0.3%-about 5.0% Compound-I (about 3 mg/mL-about 50.0 mg/mL), about 0.05% sodium phosphate monobasic monohydrate, about 2% glycerin; about 0.4% Compound-I, about 7% HPβCD, about 0.7% NaCl, about 0.005% BAK; about 0.4% Compound-I, about 4% HPβCD, about 0.7% NaCl, about 0.005% BAK; about 0.4% Compound-I, about 7% HPβCD, about 1% tromethamine, about 0.4% NaCl, about 0.005% BAK; and about 0.6% Compound-I, about 7% HPβCD, about 0.7% NaCl, about 0.005% BAK. For Compound-I of between about 0.005% to about 5.0% concentrations, cyclodextrin is present at a corresponding molar ratio.

Additional ophthalmic solutions include, for example, without being limiting: about 0.4% Formula II compound (free base), about 7.15% HPβCD, about 0.7% NaCl; about 0.1% Formula II compound (free base), about 1.79% HPβCD, about 0.85% NaCl; about 0.2% Formula II compound (free base), about 3.57% HPβCD, about 0.8% NaCl; about 0.6% Formula II compound (free base), about 10.72% HPβCD, about 0.6% NaCl; about 0.4% Formula II compound (free base), about 8.41% HPβCD, about 0.65% NaCl; about 0.4% Compound-I, about 10.51 HPβCD, about 0.65% NaCl; about 0.4% Formula II compound (free base), about 10.51% HPβCD, about 0.15% NaCl, about 1.00, tromethamine (Tris); and/or about 0.1% Formula II compound (free base), about 2.63% HPβCD, about 0.8% NaCl; about 0.6% Compound-I (as free base), about 15.77% HPβCD, about 0.37% NaCl. For Formula II of between about 0.005% to about 5.0% concentrations, cyclodextrin is present at a corresponding molar ratio.

In some embodiments, the ophthalmic solutions of Compound-I include between about 1.0%-about 25% cyclodextrin. For example, without being limiting, the Compound-I formulations include about 2.0%-about 3.0% HPβCD, about 3.0%-about 5.0% HPβCD, about 5.0%-about 10% HPβCD, or about 10%-about 25% HPβCD.

In additional embodiments, the ophthalmic solutions of Compound-I or its free base is formulated as, for example, without being limiting: about 8.41% KLEPTOSE® HPB and about 0.142% phosphate; about 8.9% KLEPTOSE® HPB and about 0.142% phosphate; about 4.88% CAPTISOL® and about 0.142 phosphate; and/or about 4.88% CAPTISOL® and about 0.122% phosphate.

In some embodiments, the ophthalmic solutions comprising cyclodextrins are clear and colorless, and are extremely viscous, moderately viscous, or have viscosity similar to water.

In some embodiments, the ophthalmic solution of the invention has a pH value of about 4.5 to about 7.5 at or under about 40° C.

For example, the ophthalmic solution of the invention has a pH value of about 6.0 at or under about 40° C.

In some embodiments, the ophthalmic solution of the invention has a pH value of about 5.0 to about 7.0 at or under about 40° C.

The ophthalmic solutions of the present disclosure contain various additives incorporated ordinarily, such as buffering agents (e.g., phosphate buffers, borate buffers, citrate buffers, tartrate buffers, acetate buffers, amino acids, sodium acetate, sodium citrate and the like), tonicity agents (e.g., saccharides such as sorbitol, glucose and mannitol, polyhydric alcohols such as glycerin, concentrated glycerin, PEG and Propylene glycol, salts such as sodium chloride, etc.), preservatives or antiseptics (e.g., Benzalkonium chloride, Benzatkonium chloride, P-oxybenzoates such as Methyl p-oxybenzoate or Ethyl p-oxybenzoate, Benzyl alcohol, Phenethyl alcohol, Sorbic acid or its salt, Thimerosal, Chlorobutanol, etc.), solubilizing aids or stabilizing agents (e.g., water-soluble polymers such as polyvinyl pyrrolidone, surfactants such as tyloxapol, polysorbates, etc.), pH modifiers (e.g., Hydrochloric acid, Acetic acid, Phosphoric acid, Sodium hydroxide. Potassium hydroxide, Ammonium hydroxide and the like), thickening agents (e.g., HEC, Hydroxypropyl cellulose, Methyl cellulose, HPMC, Carboxymethyl cellulose and their salts), chelating agents (e.g., sodium edetate, sodium citrate, condensed sodium phosphate etc.).

The ophthalmic solutions comprising cyclodextrin of the present disclosure, further comprise additional excipients, for example, without being limiting, about 0.5%-about 3% surfactant and emulsifier, for example, without being limiting, polysorbate 80 or equivalent excipients thereof; about 0.05-about 0.4% nonionic liquid polymer of the alkyl aryl polyether alcohol type, for example, without being limiting tyloxapol; and/or about 0.05%-about 0.6% hydrophilic nonionic surfactant, for example, without being limiting, poloxamer, such as poloxamer 407.

Concentration in Various Ocular Tissues-Delivered as an Ophthalmic Solution

The ocular solution comprising cyclodextrin improves bioavailability of the active agents of the current invention at the posterior segment of the eye. Without being bound by theory, in an embodiment, the formulation comprising cyclodextrin forms a clear and colorless solution, which lowers corneal exposure of the active agent, for example, exposure of Compound-I, by about 5-15 fold compared to the corneal exposure to with an equimolar Gel Drop formulation.

Without being bound by theory, in one embodiment, an ophthalmic solution comprising cyclodextrin increases the therapeutic index of Compound-I during topical ocular administration. Upon administration, the hydrophilic complex of cyclodextrin-Compound-I is pharmacologically inert at the cornea. Without being bound by theory, in some embodiments, the cyclodextrin-Compound-I complex increases corneal tolerability of Compound-I. Without being bound by theory, in some embodiments, spontaneous dissociation of cyclodextrin from Compound-I at the peripheral vasculature increases bioavailability at the target tissue, e.g., at the choroid or retina.

Unlike other formulations of Compound-I, which in some embodiments contribute to corneal toxicity, the cyclodextrin-based ophthalmic solution comprising similar concentration of Compound-I lower corneal exposures and, thereby increase the therapeutic index and corresponding benefits to patients. In one embodiment, the use of cyclodextrin-based solution of Compound-I provides approximately 10× reduction in corneal exposure, as compared to equimolar concentrations of Gel Drop. In some embodiments, the cyclodextrin-based solution of Compound-I reduces corneal exposure of Compound-I by 5×, 20×, 30×, 40×, or 50×. In one embodiment, 1-90 days or 3-9 months of topical ocular dosing of about 0.005%-about 5.0% Compound-I as a cyclodextrin-based solution does not have any adverse or toxic effect at the cornea, choroid, and/or the retina. In yet another embodiment, 1-90 days of topical ocular dosing of about 0.6%-about 5.0% Compound-I as a cyclodextrin-based solution does not have any adverse or toxic effect at the cornea, choroid, and/or the retina.

The lowering of the corneal exposure is correlated with increasing bioavailability and therapeutic index of the active agent at the posterior segment, for example, at the retina or choroid, of the eye. For example, no toxic effect attributable to the active agent or a suitable carrier is observed to the cornea or other parts of the eye when about 0.1%-about 5.0% Compound-I formulation comprising cyclodextrin is administered topically administered to the eye for at least 30 days or more than 60 days.

In one embodiment, when a formulation comprising about 0.4% (about 4 mg/mL) of Compound-I or its free base, and cyclodextrin, when administered topically to the eye, the central choroid concentration is between about 0.2 µM-about 0.9 µM, central retina concentration of the active agent is between about 0.02 µM-about 0.4 µM, aqueous humor concentration of the active agent is about 0.003 µM-about 0.009 µM, and corneal concentration of the active agent is between 6 µM-30 µM. The cyclodextrin used in the formulation is, for example, without being limiting example, KLEPTOSE® HPB or CAPTISOL®.

In some embodiments, a cyclodextrin-based solution of Compound-I or its free base increases the bioavailability of the active agent at the central choroid and the central retina, while reducing concentration at the cornea. In some embodiments, topical delivery of Compound-I or its free base formulated in the presence of cyclodextrin reduces the corneal concentration by about 5-about 15 fold over the corneal concentration of equimolar Gel Drop.

Without being bound by theory, in some embodiments, the combined effects of decreasing corneal drug exposure so as to avoid poor ocular tolerability while increasing posterior segment bioavailability increase the therapeutic index and corresponding benefits to patients.

In some embodiments, the exposure time of Compound-I is between 1 and 90 days. In some embodiments, the dosage regimen involves several courses of topical ocular administration of a formulation comprising Compound-I to a subject for between 1 and 90 days. For example, the dosage regimen involves once daily, twice daily, three times daily or four times daily administration of the formulation for between 1 and 90 days. For example, the dosage regimen involves once, twice, three times, or four times administration of the formulation on alternate days (i.e., on day 1, 3, 5, 7 etc.) for up to 90 days. For example, the dosage regimen involves administering once on day 1, once or twice on day 2-day 90. For example, the dosage regimen involves administering once, twice, three times, or four times on day 1, followed by once daily for 2-90 days. For example, the dosage regimen involves administering once, twice, three times, four times on day 1, followed by once, twice, three times, or four times on alternate days (i.e., on day 1, 3, 5, 7 etc.) for up to 90 days. For example, one dosage regimen involves once per day or twice per day for 1, 2, 3, 4, or 5 consecutive days. For twice or three daily dosage regimen, subjects receive topical ocular dose of a Compound-I formulation on days 1 and 4 approximately about 4, 6, or 8 hours apart. In another embodiment, subjects receive topical ocular doses of a Compound-I formulation approximately about 4, 6, or 8 hours apart for four consecutive days. In some embodiments, subjects receive one or two doses of topical ocular dose of Compound-I formulation per day for 5 consecutive days. In yet other embodiments, subjects receive one or two doses of topical ocular dose of Compound-I formulation for 5-90 consecutive days. In some embodiments, subjects receive one or two doses of topical ocular dose of Compound-I formulation for at least 25 consecutive days. In one embodiment, subjects receive one or two topical ocular doses for at least 90 consecutive days or more.

For example, a formulation comprising about 2 mg/mL BID of Compound-I is administered to one eye or both eyes of a subject for between 1 and 90 days. In some embodiments a formulation comprising about 3 mg/mL BID of Compound-I is administered to one eye or both eyes of a subject for between 1 and 90 days. In some embodiments a formulation comprising about 3 mg/mL QD of Compound-I is administered to one eye or both eyes of a subject for between 1 and 90 days. In some embodiments a formulation comprising about 4 mg/mL BID of Compound-I is administered to one eye or both eyes of a subject for between 1 and 90 days. In some embodiments a formulation comprising about 4 mg/mL QD of Compound-I is administered to one eye or both eyes of a subject for between 1 and 90 days. In some embodiments a formulation comprising about 5 mg/mL BID of Compound-I is administered to one eye or both eyes of a subject for between 1 and 90 days. In some embodiments a formulation comprising about 5 mg/mL QD of Compound-I is administered to one eye or both eyes of a subject for between 1 and 90 days. In some embodiments a formulation comprising about 6 mg/mL BID of Compound-I is administered to one eye or both eyes of a subject for between 1 and 90 days. In some embodiments a formulation comprising about 6 mg/mL QD of Compound-I is administered to one eye or both eyes of a subject for between 1 and 90 days. The dosage regimen for between 1 and 90 days may be any of the regimens involving consecutive or alternate days described in the paragraph above.

The present disclosure provides cyclodextrin-based solutions containing hydroxypropyl-beta-cyclodextrin (HP-β-CD, KLEPTOSE® HPB) or CAPTISOL® that are well tolerated when administered topically for 30-90 days or for 4-6 months. In some embodiments, once or twice daily administration of at about 0.005%-about 5.0% w/v Compound-I or its free base in a solution containing about 1.0%-about 25% HP-β-CD or CAPTISOL® is well tolerated by the subject.

In some embodiments, the formulation of Formula (II) or Compound-I is administered to one eye or both eyes of a subject. For example, about 0.2%-about 0.6% (w/v) of the compound of Formula (II) or about 0.1%-0.7% (w/v) of Compound-I comprising formulation of the current disclosure is administered once a day (QD) or twice a day (BID)

to one eye or both eyes of a subject for between 1 and 90 days. In some embodiments, Formula (II) compound or Compound-I is complexed with a complexing agent, e.g., cyclodextrin (e.g., KLEPTOSE® HPB (%)) in ratio of about 1:8, in which about 2%-13% (w/v) cyclodextrin (e.g., KLEPTOSE® HPB (%)) is added to the formulation. The formulation further comprises about 0.1%-about 0.2% buffer, e.g., 10 mM phosphate buffer. The desired osmolality of the formulation is about 200-about 300 mOsm, achieved by adding quantity sufficient to achieve the osmolality with a salt, e.g., sodium chloride. The pH of the formulation is about 6.0 at or under about 40° C. The dosage regimen for between 1 and 90 days may be any of the regimens involving consecutive or alternate days described in the paragraph above.

Ophthalmic Suspensions

The current embodiments provide suspensions of Compound-I including the compound and pharmaceutically acceptable excipients. For example, Compound-I suspensions include, without being limiting, buffering agents, acids & bases, for example, without being limiting, HCl and NaOH. In one embodiment, suspensions of Compound-I or its free base include buffering agent, for example, without being limiting, tromethamine (Tris). The tromethamine-based suspension of Formula II compound or Compound-I is useful for topical administration to the eye.

The suspensions of the invention comprise about 0.005% to about 5.0% w/v of an active agent of Formulae (I), (II), or a pharmaceutically acceptable salt thereof, for example, Compound-I. The concentration of Compound-I or its free base (formula II) in the suspensions is about 0.005%-about 0.01%, about 0.01%-about 0.05%, about 0.05%-about 0.1%, about 0.1%-about 0.2%, about 0.2%-about 0.3%, about 0.3%-about 0.4%, about 0.4%-about 0.5%, about 0.5%-about 0.6%, about 0.6%-about 0.7%, about 0.7%-about 0.8%, about 0.8%-about 0.9%, about 0.9%-about 1.0%, about 1.0-about 2.0%, about 2.0-about 3.0%, about 3.0-about 4.0%, or about 4.0-about 5.0% w/v for topical administration. In some embodiments, the suspensions include about 0.005%, about 0.05%, about 0.1%, about 0.2%, about 0.3%, about 0.4%, about 0.5%, about 0.6%, about 0.7%, about 0.8%, about 0.9%, about 1.0%, about 2.0%, about 3.0%, about 4.0%, or about 5.0% w/v of Compound-I or its free base (formula II).

The ophthalmic suspensions may contain various additives incorporated ordinarily, such as buffering agents (e.g., phosphate buffers, borate buffers, citrate buffers, tartrate buffers, acetate buffers, amino acids, sodium acetate, sodium citrate and the like), tonicity agents (e.g., saccharides such as sorbitol, glucose and mannitol, polyhydric alcohols such as glycerin, concentrated glycerin, PEG and propylene glycol, salts such as sodium chloride), preservatives or antiseptics (e.g., benzalkonium chloride, benzatkonium chloride, P-oxybenzoates such as methyl p-oxybenzoate or ethyl p-oxybenzoate, Benzyl alcohol, phenethyl alcohol, Sorbic acid or its salt, Thimerosal, Chlorobutanol and the like), solubilizing aids or stabilizing agents (e.g., cyclodextrins and their derivative, water-soluble polymers such as polyvinyl pyrrolidone, surfactants such as tyloxapol, polysorbates), pH modifiers (e.g., hydrochloric acid, acetic acid, phosphoric acid, sodium hydroxide, potassium hydroxide, ammonium hydroxide and the like), thickening agents (e.g., HEC, hydroxypropyl cellulose, methyl cellulose, HPMC, carboxymethyl cellulose and their salts), chelating agents (e.g., sodium edetate, sodium citrate, condensed sodium phosphate) and the like.

The ophthalmic suspension of the current invention includes pharmaceutical excipients chosen at or below concentrations optimal for ophthalmic solution. The excipients of the current invention include, for example, without being limiting, sodium phosphate monohydrate, glycerin, and benzalkonium chloride (BAK).

In some embodiments, about 0.005%, about 0.05%, about 0.1%, about 0.2%, about 0.3%, about 0.4%, about 0.5%, about 0.6%, about 0.7%, about 0.8%, about 0.9%, about 1.0%, about 2.0%, about 3.0%, about 4.0%, or about 5.0% w/v of Formulae (I), (II), or a pharmaceutically acceptable salt thereof, for example, Compound-I, is an aqueous tromethamine solution. The tromethamine-based suspension of Compound-I or its free base includes additional buffers and excipients, for example, without being limiting, phosphate buffer. The suspensions prepared in about 0.2%-about 1.0% Tris may further comprise one or more surfactant and emulsifier, for example, without being limiting, polysorbate 80 or equivalent excipients thereof; one or more nonionic liquid polymer of the alkyl aryl polyether alcohol type, for example, without being limiting tyloxapol; and/or one or more hydrophilic non-ionic surfactant, for example, without being limiting, poloxamer, such as poloxamer 407.

The present disclosure provides suspensions of the agents of the current invention formulated in the presence of excipients such as, without being limiting, Povidone, polysorbate 80 (PS80), polyethylene glycol (PEG) 400, tyloxapol, poloxamer, glycerin, and BAK in a Tris buffer.

In one embodiment the suspension of Compound-I or its free base comprises about 0.1-0.5% phosphate buffer. In some embodiments, the pH of the tromethamine-based suspension is between pH 4-7, for example, pH 6.0. In some embodiments, the suspensions prepared in Tris further comprise about 0.5%-about 2% polysorbate 80; about 0.05-about 0.2% tyloxapol; and/or about 0.05%-about 0.4% poloxamer 407.

In some such embodiments, the suspensions of the invention further comprise about 0.01-about 1%, or about 1-about 2.0% w/v glycerin. In a specific embodiment, the suspensions comprise about 2% w/v glycerin.

In some embodiments, the suspensions of the invention further comprise about 0.001-about 0.005% w/v Benzalkonium chloride (BAK). The BAK amount may be varied depending on any observed adverse effects. BAK may be damaging to the cells on the ocular surface, and, therefore, the amount in the formulation may be varied to achieve an optimal level of ocular penetration of Compound-I, without compromising the ocular cell layer integrity and increased toxicity.

In some embodiments, the suspension optionally comprises buffers. Buffers when used, for example, can be sodium monophosphate basic, phosphoric acid and Tris buffer. Compound-I concentration in suspension is about 0.005%-about 5.0% w/v. The suspension prepared without additional buffer further comprises about 0.005% BAK and about 2% glycerin and with a pH 6.0. In another embodiment the suspension prepared without additional buffer comprises about 1% polysorbate 80, about 0.1% tyloxapol, about 0.2% Poloxamer 407, about 0.005% BAK, about 2.0% glycerin, and with a pH 6.0.

In suspensions prepared in phosphoric acid/Tris, the suspension comprises about 0.14% phosphoric acid, about 0.2% Tris base, about 1.0% polysorbate 80, about 0.005% BAK, about 2.0% glycerin and with a pH 6.0. In one embodiment, the suspension further comprises about 0.2% tyloxapol. The pH of the suspension varies between about pH 6.0 and 7.2.

The suspensions prepared in tromethamine (Tris) alone comprise about 1% polysorbate 80, about 0.1% tyloxapol, about 0.2% Poloxamer 407, about 0.6% Tris, about 0.005% BAK, and about 2.0% glycerin with pH 6.0. In another embodiment, a suspension prepared in Tris comprises, about 1% Tris, about 0.45% NaCl, about 0.025% EDTA, about 0.2% HPMC, about 0.1% polysorbate 80, about 0.005% BAK, with a pH 6.0. In these suspensions 1 N HCl and/or 1N NaOH are used for titration to appropriate pH.

The suspension of the invention comprises about 0.005%, about 0.05%, about 0.1%, about 0.2%, about 0.3%, about 0.4%, about 0.5%, about 0.6%, about 0.7%, about 0.8%, about 0.9%, about 1.0%, about 2.0%, about 3.0%, about 4.0%, or about 5.0% of an active agent of Formulae (I), (II), or a pharmaceutically acceptable salt thereof, for example, Compound-I, and about 0.01%-about 0.05%, about 0.05-about 0.09%, or about 0.09-about 0.2% w/v sodium phosphate monobasic monohydrate and/or about 0.3%-about 1.0% of Tris. In a specific embodiment, the suspension comprises about 0.14% or about 0.2% w/v Tris-buffer. In additional embodiments, suspensions are prepared in about 0.6% Tris or about 1.0% Tris. Other equivalent buffer systems well known in the art are also used in the suspensions of the current invention. In one embodiment, the Formula II compound or Compound-I is formulated as about 0.4% active agent, about 5% Cremophor RH40, about 2.0% glycerin, and about 0.005% BAK.

In some embodiments, the suspension of the invention has a pH value of about 4.0 to 7.5 at or under about 40° C.

For example, the suspension of the invention has a pH value of about 6.0 at or under about 40° C.

In some embodiments, the suspension of the invention has a pH value of about 5.0 to about 7.0 at or under about 40° C.

Concentration in Various Ocular Tissues—Delivered as an Ophthalmic Suspension

In some embodiments, suspension of Compound-I or its free base provides similar concentration of the active agent at the central choroid and the central retina compared to the concentration of the active agent delivered in Gel Drop form (discussed infra).

In some embodiments, Tris-based suspension of Compound-I or its free base increases the bioavailability of the active agent at the central choroid and the central retina, while reducing concentration at the cornea. In some embodiments, topical delivery of Compound-I or its free base formulated in Tris-base reduces corneal concentration by about 5-10×, 10-20×, 20-30×, 30-40×, or about 50-100× compared to the corneal concentration of equimolar Compound-I or its free base delivered as a Gel Drop.

The combined effects of decreasing corneal drug exposure so as to avoid poor ocular tolerability while maintaining or increasing posterior segment bioavailability so as to increase inhibition of receptor tyrosine kinase (RTK), for example, VEGF, significantly increases the therapeutic index and corresponding benefits to patients.

Once or twice daily administration of about 0.005%-about 5.0% w/v Compound-I suspension of the current invention for 30-90 days or 4-6 months is well tolerated in the eye.

Gel Drop

In some embodiments the ophthalmic composition or formulation of the current invention is formulated as a Gel Drop. The Gel Drop formulation includes no more than about 0.05% of sodium phosphate monobasic monohydrate to provide the required buffering capacity and free-flowing, filterable formulations at about 0.005%-about 2.0%0 Compound-I without the need for surfactant additives.

The Gel Drop formulation of the invention comprises about 0.005% to about 2.0% w/v of the active agent of Formulae (I), (II), or a pharmaceutically acceptable salt thereof, for example, Compound-I. The concentration of Compound-I or its free base (formula II) in the Gel Drops may be about 0.005%-about 0.01%, about 0.01%-about 0.05%, about 0.05%-about 0.1%, about 0.1%-about 0.2%, about 0.2%-about 0.3%, about 0.3%-about 0.4%, about 0.4%-about 0.5%, about 0.5%-about 0.6%, about 0.6%-about 0.7%, about 0.7%-about 0.8%, about 0.8%-about 0.9%, about 0.9%-about 1.0%, or about 1.0%-about 2.0% w/v for topical administration. In some embodiments, the Gel Drops include about 0.005%, about 0.05%, about 0.1%, about 0.2%, about 0.3%, about 0.4%, about 0.5%, about 0.6%, about 0.7%, about 0.8%, about 0.9%, about 1.0%, or about 2% w/v of Compound-I or its free base (formula II).

In some embodiments, the Gel Drop ophthalmic composition of the current invention includes glycerin as a tonicity agent. Some embodiments of the invention provide ophthalmic composition including mannitol. The glycerin or mannitol content at an amount to prevent any changes in the solubility of Compound-I, and at a level of about 2.0-about 2.5%, glycerin provides an osmolality of about 225-about 300 mOsm/kg depending on the phosphate concentration. In additional embodiments, glycerin is about 2% and phosphate is about 0.05% of the gel drop ophthalmic composition. The concentrations of glycerin and phosphate of the current invention is in an amount that the tonicity level of the ophthalmic composition is about 240 mOsm/kg.

The Gel Drop ophthalmic composition of the current invention includes Benzalkonium Chloride (BAK). In some embodiments, the BAK content is about 0.005%, sufficient for preservation of the ophthalmic composition against microbial contamination. In some embodiments of the current invention, BAK is not required for use of ophthalmic composition in a sterile, single-use product.

The Gel Drop ophthalmic formulation of Compound-I includes: about 0.005%-about 2.0%, Compound-I or its free base, about 0.05% sodium phosphate, about 2% glycerin as the tonicity adjusting agent, about 0.005% BAK as a preservative, water (purified, i.e., distilled, or deionized) as a vehicle, and sodium hydroxide to adjust pH to 6.0. In one embodiment, no other excipients are added.

The Gel Drop of the invention comprises about 0.005%-about 2.0% of the active agent of Formulae (I), (II), or a pharmaceutically acceptable salt thereof, for example, Compound-I, and about 0.01%-about 0.05%, about 0.05-about 0.09%, or about 0.09-about 0.2% w/v sodium phosphate monobasic monohydrate. In a specific embodiment, the Gel Drop comprises about 0.05%, about 0.2%, or about 0.2% w/v sodium phosphate monobasic monohydrate buffer. Other equivalent buffer systems well known in the art are also used in the Gel Drop of the current invention. In one embodiment, Compound-I or its free base is formulated as about 0.4%-about 2.0% active agent, about 5% Cremophor RH40, about 2.0% glycerin, and about 0.005% BAK.

In one embodiment, the Gel Drop of Compound-I includes about 0.3%-about 2.0% (3-20 mg/mL) Compound-I, about 0.05%-about 0.2% Sodium Phosphate, and about 2% glycerin. The pH of the composition is between pH 5.0-7.0.

The present disclosure provides Gel Drop of the agents of the current invention formulated in the presence of excipients such as, without being limiting example, Povidone, polysorbate 80 (PS80), polyethylene glycol (PEG) 400, tyloxapol, poloxamer, glycerin, and BAK in a phosphate buffer.

Eye Drops

Disclosed herein is a formulation, comprising the disclosed compounds as eye drops, a form of drug delivery that is pharmaceutically-acceptable to patients, convenient, safe, with an onset of action of several minutes. A standard eye drop used in therapy according to U.S. federal regulatory practice is sterile, have a pH of about 6.0-7.4, and, if to be used more than once, contains a preservative but has a limited shelf life after opening, usually one month. If the eye drops are packaged in a sterile, single use only unit-dose dispenser, the preservative can be omitted.

One method of eye drop formulation comprises the purest form of the disclosed compound (e.g., greater than 99% purity), and mix the compound with buffer and tonicity adjusters, to adjust for physiological pH and osmolarity. Examples of buffering agents to maintain or adjust pH include, but are not limited to, acetate buffers, citrate buffers, phosphate buffers and borate buffers. Examples of tonicity adjustors are sodium chloride, mannitol and glycerin. In some embodiments, other pharmaceutically acceptable ingredients are also added.

The formulated solution is then aliquoted into either a plurality of discrete, sterile disposable cartridges each of which is suitable for unit dosing, or a single cartridge for unit dosing. Such a single disposable cartridge is, for example, a conical or cylindrical specific volume dispenser, with a container having side-walls squeezable in a radial direction to a longitudinal axis in order to dispense the container contents therefrom at one end of the container.

The present disclosure provides ophthalmic eye-drop solutions/suspensions packaged in multi-dose form or single dose form, for example, as a plastic bottle with an eye-dropper. In multi-dose form formulations, preservatives are required to prevent microbial contamination after opening of the container. Suitable preservatives include, but are not limited to: benzalkonium chloride, thimerosal, chlorobutanol, methyl paraben, propyl paraben, phenylethyl alcohol, edetate disodium, sorbic acid, polyquatemium-1, or other agents known to those skilled in the art, and all of which are contemplated for use in the present invention. Such preservatives are typically employed at a level of from 0.001 to about 1.0% weight/volume.

Without wishing to be bound by theory, the formulation of the current invention in an eye drop provides a pulse entry of the drug. The route by which Compound-I obtains access to the posterior segment is not by direct diffusion through the cornea with subsequent diffusion through the aqueous humor, vitreous humor, retina and ultimately the choroid. Rather, the Compound-I compound achieves notable bioavailability posteriorly following topical instillation using a circumferential route around, rather than through, the globe.

In certain clinical conditions, the eye drop solutions/suspensions can be formulated with other pharmaceutical agents, in order to attenuate the irritancy of the other ingredient and to facilitate clinical response. Such agents include, but are not limited to, a vasoconstrictor such as phenylephrine, oxymetazoline, napthazoline or tetrahydrozoline; a mast-cell stabilizer such as olopatadine; an antihistamine such as azelastine; an antibiotic such as tetracycline; a steroidal anti-inflammatory drug such as betamethasone; a non-steroidal anti-inflammatory drug such as diclofenac; an immunomodulator such as imiquimod or interferons; and antiviral agents such as valaciclovir, cidofovir and trifluridine. The doses used for the above described purposes vary, but are in an effective amount to suppress discomfort, itch, irritation, or pain in the eye. When the compositions are dosed topically, the "pharmaceutically effective amount" of compound can generally be in a concentration range of from 0.05 mg/mL to about 10 mg/mL, with 1 to 4 drops administered as a unit dose 1 to 4 times per day. The most common method of ocular drug delivery is the instillation of drops into the cornea (i.e., "eye drops").

A key requirement is that the formulation be sterile and produced in a sterile environment. An ideal disclosed compound for use in ophthalmic solutions/suspensions should be soluble and/or miscible in aqueous media at normal ocular pH and tonicity. Moreover, the disclosed compounds should be stable, non-toxic, long acting, and sufficiently potent to counteract dilution of drug concentration by blinking and tearing.

Dosage Forms

The formulation of the current invention may be suitable for ophthalmic use. In one embodiment the formulation is a solution. The solution of the current invention may be a clear, colorless, sterile, isotonic, buffered aqueous free-flowing liquid preparation. The drug product has a pH of approximately 6.0 and may be stored at +5 OC. The drug product may be provided in a container closure system consisting of a semi-transparent ophthalmic dispenser bottle with a dropper tip and cap.

In some embodiments, the clinical concentration of Compound-I ophthalmic solution or suspension is equal to or less than about 0.1 mg/mL, equal to or less than about 0.2 mg/mL, about 0.2-about 1.0 mg/mL, about 0.3-about 1.0 mg/mL, about 0.4-about 1.0 mg/mL, about 0.5-about 1.0 mg/mL, about 0.6-about 1.0 mg/mL, about 0.7-about 1.0 mg/mL, about 0.8-about 1.0 mg/mL, about 0.9-about 1.0 mg/mL, about 1.0-about 2.0 mg/mL, about 2.0-about 3.0 mg/mL, about 3.0-about 4.0 mg/mL, about 4.0-about 5.0 mg/mL, about 5.0-about 6.0 mg/mL, about 5.0-about 10.0 mg/mL, about 10-about 20 mg/mL, about 20-about 30 mg/mL, about 30-about 40 mg/mL, or about 40-about 50 mg/mL.

In one embodiment of the current invention the strength of the compound is about 0.005%-about 5.0% (about 0.5-about 50 mg/mL). A desired pharmacologic activity (or concentration) of the formulation of the current invention against pathologic choroidal and retinal neovascularization is achieved following ocular administration of formulations containing about 0.005%, about 0.05%, about 0.1%, about 0.2%, about 0.3%, about 0.4%, about 0.5%, about 0.6%, about 0.7%, about 0.8%, about 0.9%, about 1.0%, about 2.0%, about 3.0%, about 4.0%, or about 5.0% w/v of Compound-I. The current invention provides that, following topical ocular administration with an optimal dose (for example, between about 0.005% and about 5.0%) the pharmacologically active concentration is achieved and maintained in the central choroid target tissue. In one embodiment the active agent (Formula II or Compound-I) is formulated as about 0.005-about 5.0% w/v concentration and is dosed once or twice a day per eye for more than 60 consecutive days. The plasma concentrations observed following topical administration are substantially below the level expected to produce systemic toxicity.

TABLE 2

| In vitro Summary of pharmacodynamic properties for Compound-I | |
|---|---|
| In Vitro Assay | $IC_{50}$ = nM (ng/mL) |
| Inhibition of recombinant VEGFR-2 tyrosine kinase using exogenous substrate | 10.55 (6) |
| Inhibition of recombinant FGFR-2 tyrosine kinase using exogenous substrate | 8.79 (5) |

TABLE 2-continued

In vitro Summary of pharmacodynamic properties for Compound-I

| In Vitro Assay | IC$_{50}$ = nM (ng/mL) |
|---|---|
| Inhibition of recombinant PDGFR tyrosine kinase using exogenous substrate | 2636.67 (1500) |
| Inhibition of recombinant EGFR tyrosine kinase using exogenous substrate | 5853.40 (3330) |
| Inhibition of recombinant IR tyrosine kinase using exogenous substrate | 10283.00 (5850) |
| Inhibition of VEGF-stimulated VEGFR-2 autophosphorylation in intact cells | 5.27 (3) |
| Inhibition of VEGF-stimulated mitogenesis in HUVECs | 14.06 (8) |

In some embodiments, Compound-I exhibits potent inhibition of tyrosine kinase activity for several proangiogenic growth factor receptors, with IC$_{50}$ of less than about 100 nM (see Table 3). Compound-I also blocks the high-affinity VEGF receptors, e.g., VEGFR-1/Flt-1, but with lower potency (with IC$_{50}$ of about 122 nM (69.41 ng/mL)).

TABLE 3

In Vitro Inhibition of Tyrosine Kinases using a 10-point Titration Curve (257 nM-5000 nM) or Compound-I

| Kinase | IC$_{50}$ – nM (ng/mL) for Compound-I |
|---|---|
| AURKB (Aurora B) | 207 (117.76) |
| FGFR-1 | 8.50 (4.84) |
| FGFR-2 | 3.08 (1.75) |
| FGFR-3 | 33.9 (19.29) |
| FGFR4 | 500 (284.45) |
| FLT1 (VEGFR-1) | 122 (69.41) |
| FLT3 | 419 (238.37) |
| FLT4 (VEGFR-3) | 54.2 (30.83) |
| FYN | 161 (91.59) |
| KDR (VEGFR-2) | 1.27 (0.72) |
| PDGFRA (PDGFR alpha) | 3120 (1774.97) |
| PDGFRB (PDGFR beta) | 1860 (1058.16) |
| TEK (Tie2) | 10.1 (5.75) |
| RET | 11.1 (6.31) |

Although VEGFR inhibition appears to be essential for reducing vascular permeability and preventing further neovascular growth, the simultaneous inhibition of VEGF signaling with inhibition of other growth factor signaling pathways (e.g., PDGF and angiopoietins/Tie2) may be linked to unique therapeutic outcomes. The therapeutic outcomes of a broader inhibition of signaling pathways may contribute to the regression of newly established pathologic vessels in the posterior segment of the eye.

In some embodiments, about 300 nM (about 170.67 ng/mL) of Compound-I inhibits VEGFR-2 kinase function (see Table 4). Substantial blockade of a similar set of proangiogenic growth factor receptors, including FGFRs1-3, Tie-2, and EphB-4 are also observed. An unexpected finding is that about 300 nM concentration of Compound-I inhibits the VEGFR-2 kinase function, which falls within the typical range found in the central choroid and retina following five days of topical ocular delivery.

TABLE 4

In Vitro Inhibition of Tyrosine Kinases by 300 nM (170.67 ng/mL) Compound-I

| Kinase | Mean % Inhibition at 300nM Compound-I |
|---|---|
| EPHB-4 | 87 |
| FGFR-1 | 96 |
| FGFR-2 | 103 |
| FGFR-3 (K650E variant) | 104 |
| FLT4 (VEGFR-3) | 86 |
| KDR (VEGFR-2) | 104 |
| RET | 98 |
| RET (Y791F mutation) | 97 |
| TEK (Tie2) | 96 |

TABLE 5

In vitro Inhibition of Tyrosine Kinases by 1 μM (568.9 ng/mL) Compound-I

| Kinase | Mean % Inhibition at 1 μM Compound-I |
|---|---|
| ABL1 | 92 |
| ABL1 E255K | 90 |
| ABL1 G250E | 89 |
| ABL1 T315I | 101 |
| ABL1 Y253F | 93 |
| ACVR1B (ALK4) | 98 |
| AURKB (Aurora B) | 82 |
| BRAF V599E | 85 |
| EPHA-1 | 81 |
| EPHA-8 | 85 |
| EPHB-1 | 83 |
| EPHB-4 | 80 |
| FGFR-1 | 98 |
| FGFR-2 | 99 |
| FGFR-3 | 96 |
| FGFR-3 K650E | 100 |
| FGR | 91 |
| FLT-1 (VEGFR-1) | 86 |
| FLT-4 (VEGFR-3) | 95 |
| KDR (VEGFR-2) | 98 |
| LCK | 97 |
| LYN A | 81 |
| LYN B | 91 |
| MAP4K4 (HGK) | 100 |
| MAP4K5 (KHS1) | 94 |
| MAPK14 (p38 alpha) | 86 |
| MINK1 | 100 |
| PDGFRA T674I | 86 |
| PTK6 (Brk) | 88 |
| RET | 98 |
| RET Y791F | 94 |
| SNF1LK2 | 82 |
| SRC | 91 |
| SRC N1 | 83 |
| TEK (Tie2) | 99 |
| YES1 | 98 |

Overview of Drug Substance and Drug Product

Drug Product: Compound-I Ophthalmic formulations for clinical studies are manufactured in dosage strengths between 0.05%-1.0% (as Compound-I). In some embodiments, Compound-I dosage in the formulation is 0.05%, 0.1%, 0.2%, 0.3%, 0.4%, 0.6%, 0.8%, or 1.0%. Compound-I Ophthalmic Formulations (solutions or suspensions) are for daily, single use, topical administration to the eye in a clinical setting. In addition to the active ingredient, in some embodiments the drug product contains about 0.005% BAK as a preservative, purified water as vehicle, and is pH-adjusted with sodium hydroxide to pH 6.0.

Sodium Phosphate-Based Gel Drop

The ophthalmic benefits of Compound-I in a sodium phosphate-based formulation (listed in Table 6) results from the self-gelling properties of the API in buffers, such as sodium phosphate. Spontaneous formation of self-forming, thixotropic gel of Compound-I from a clear solution is formed by increasing active agent concentration in sodium phosphate. Once the active agent concentration in the phosphate buffer reaches super-saturated state, insoluble particulates of Compound-I are observed within the gel.

The current state of the art predicts that application of a gel with increased viscosity to the surface of the eye would increase corneal residence time. Increased corneal residence time in turn facilitates ocular drug absorption. As a result, the intraocular drug concentrations of viscous gels would be increased in comparison to non-viscous formulations, such as water-like solutions. One way to increase viscosity is to use various viscosity-enhancing excipients, e.g., carboxymethylcellulose, which in effect achieves increased intraocular absorption of different drug substances following topical ocular administration. The present disclosure provides a thixotropic gel of Compound-I formed in the absence of any viscosity-enhancing excipients. For example, when Compound-I is dissolved into a simple buffer, such as sodium phosphate, a thixotropic gel is formed. The thixotropic gel, which is formed without any viscosity-enhancing excipients, is formulated as a Gel Drop.

The present disclosure provides dose-dependent and dose-frequency dependent delivery of Compound-I to the posterior segment eye tissues.

The Gel Drop formulations of the present disclosure (listed in Table 6) differ among each other in several aspects, such as active concentration, sodium phosphate concentration, presence or absence of tonicity (glycerin) or preservative (benzalkoniumchloride/BAK) agents, solubilizing surfactants (polysorbate 80, tyloxapol, and/or poloxamer), and pH.

Tromethanine-Based Suspension

The present disclosure provides a suspension of Compound-I in a tromethamine-based formulation. In some embodiments, the suspension of Compound-I in a tromethamine-based formulation has equal to or more than 95% of the active drug substance in an insoluble form. This characteristic is distinguishable from the soluble or semi-soluble state of Compound-I in the Gel Drop (the Gel Drop (gel), which is not an entirely soluble state as concentration of the active agent increases) or in a Cyclodextrin-based formulation. Tromethamine-based formulations of Compound-I show increased turbidity with increasing active agent concentration. Administering a topical drop of Compound-I suspension to the eye, which is a combination of soluble and insoluble active agent components, are beneficial with respect to both safety/tolerability and efficacy.

The present disclosure provides Compound-I in the tromethamine-based suspension, delivered at concentrations to the target tissues between 10-1000× of the cellular $IC_{50}$ for the various pro-angiogenic RTKs. See, e.g., Table 7.

The corneal safety and tolerability of topical Compound-I is a direct consequence of the amount of soluble (as opposed to insoluble) active agent applied to the corneal surface, and the resultant corneal tissue concentration. In some embodiments, subjects who receive topical ocular administration of the tromethamine-based suspension are able to tolerate up to higher level of the active agent concentration in the formulation, as compared to equimolar formulations of the sodium phosphate-based Gel Drop.

TABLE 6

PK results with topical ocular formulation of Compoundil in Sodium Phosphate-based Gel Drop

| CD* mg/ml | pH | Phos % | BAK % | Gly % | PS80 % | Tylox % | Polox % | Osmo |
|---|---|---|---|---|---|---|---|---|
| 6 | 5.9 | 0.05 | 0.005 | 2 | 1 | 0.1 | 0.2 | 270 |
| 5 | 6 | 0.2 | 0.005 | 2 | | | | 273 |
| 6 | 5.9 | 0.15 | | | | | | 80 |
| 6 | 6.1 | 0.05 | 0.005 | 2 | 1 | 0.1 | | 248 |
| 6 | 5.9 | 0.1 | 0.005 | 2 | | | 0.2 | 257 |
| 4 | 6.0 | 2 | 0.005 | 2 | 1 | 0.2 | | |
| 2 | 6.1 | 0.05 | 0.005 | 2 | 1 | 0.1 | | 239 |
| 5 | 6 | 0.2 | 0.005 | 2 | 1 | | 0.2 | 288 |
| 2 | 6.0 | 0.02 | 0.005 | 2 | 1 | 0.2 | | |
| 4 | 6.0 | 0.2 | 0.005 | 2 | | | | |
| 2 | 6 | | 0.005 | 2 | | | | 232 |
| 2 | 6 | 0.05 | 0.005 | 2 | 1 | | | 261 |
| 1 | 6.1 | | 0.005 | 2 | | | | 230 |
| 2 | 6.0 | 0.2 | 0.005 | 2 | | | | |
| 2 | 6.0 | 0.05 | 0.005 | 2 | | | | |
| 2 | 6.0 | 0.1 | 0.005 | 2 | | | | |
| 1 | 6.0 | 0.2 | 0.005 | 2 | | | | |
| 2 | 6.1 | 0.15 | | | | | | 34 |
| 2 | 6.1 | | 0.005 | 2 | | | | 229 |
| 1 | 6.0 | 0.2 | 0.005 | 2 | 1 | 0.2% | | |
| 2 | 6 | 0.05 | 0.005 | 2 | | | | 244 |
| 1 | 6 | 0.05 | 0.005 | 2 | | | | |
| 2 | 5.9 | 0.05 | 0.005 | 2 | | | | 233 |
| 1 | 6 | | 0.005 | 2 | | | | 234 |
| 2 | 6 | 0.2 | 0.005 | 2 | 1 | | | 281 |
| 2 | 6.1 | 0.15 | | | | | | 22 |
| 2 | 6.0 | 0.05 | 0.005 | 2 | 1 | 0.2 | | |
| 1 | 6 | | 0.005 | 2 | 1 | 0.1 | 0.2 | 237 |
| 2 | 6 | 0.2 | 0.005 | 2 | | | | 257 |
| 1 | 6.0 | 0.05 | 0.005 | 2 | 0.01 | 0.2 | | |
| 1 | 6 | 0.05 | 0.005 | 2 | 1 | | | 254 |

TABLE 6-continued

PK results with topical ocular formulation of Compoundi1 in Sodium Phosphate-based Gel Drop

| Days Dosing | Dose x per Day | MEAN [choroid] nM | SD [choroid] nM | Mean [retina] nM | SD [retina] nM | Mean [AH] nM | SD [AH] nM | [plasma] nM |
|---|---|---|---|---|---|---|---|---|
| 4 | 3x | 22.40 | | | | 222 | | 15.6 |
| 5 | 3x | 1160 | | | | 50.9 | | 12.5 |
| 4 | 3x | 823 | | | | | | |
| 5 | 3x | 779 | | | | | | |
| 4 | 3x | 768 | | | | 55.4 | | 8.43 |
| 5 | 3x | 760 | 150 | 97.6 | 30.2 | 21.1 | 8.24 | 8.06 |
| 5 | 3x | 660 | | | | | | |
| 5 | 3x | 612 | | | | | | |
| 5 | 3x | 599 | 225 | 92.9 | 28.6 | 13.8 | 3.04 | 4.46 |
| 5 | 3x | 596 | 105 | 68.3 | 53.4 | 25 | 5.4 | 5.84 |
| 5 | 3x | 589 | | <LLoQ | | 30 | | 5.41 |
| 5 | 3x | 559 | | 126 | | 25.5 | | 4.15 |
| 5 | 3x | 537 | | | | | | |
| 5 | 3x | 532 | 238* | 34.8 | 69.5 | 14.8 | 1.81 | 4.47 |
| 5 | 3x | 528 | 106 | 113 | 42.7 | 32.2 | 11.3 | 5.79 |
| 5 | 3x | 525 | 51.3 | 42.9 | 50.5 | 18.9 | 5.69 | 5.71 |
| 5 | 3x | 519 | 44.4 | 90.8 | 20.8 | 20.6 | 4.16 | 3.97 |
| 4 | 3x | 466 | | | | 13.7 | | 4.81 |
| 5 | 3x | 462 | | | | | | |
| 5 | 3x | 423 | 34.1 | 32.7 | 37.8 | 6.27 | 1.06 | 2.89 |
| 5 | 3x | 422 | | 121 | | 27.8 | | 5.92 |
| 5 | 3x | 398 | 81.6 | 101 | 30.1 | 16.4 | 6.08 | 4.45 |
| 5 | 3x | 362 | | | | | | |
| 5 | 3x | 359 | | | | 17.1 | | |
| 5 | 3x | 357 | | 102 | | 19.7 | | 4.94 |
| 5 | 3x | 356 | | | | | | |
| 5 | 3x | 349 | 44.1 | 85.7 | 19.6 | 18.2 | 6.91 | 4.36 |
| 5 | 3x | 339 | | | | | | |
| 5 | 3x | 316 | | <LLoQ | | 29.5 | | 5.26 |
| 5 | 3x | 295 | 48.7 | 46.8 | 54.1 | 9.09 | 0.989 | 3.49 |
| 5 | 3x | | | | | | | |

*CD: Compound 1

TABLE 7

PK results with topical ocular Compound-I in tromethamine-based suspension

| CD* mg/mL | pH | Phos % | Tris | BAK % | Gly % | PS80 % | Tylox % | Polox % | Osmo |
|---|---|---|---|---|---|---|---|---|---|
| 10 | 6 | 0.14 | 1 | 0.005 | 2 | | | | 414 |
| 5 | 6.0 | 0.14 | ~0.20 | 0.005 | 2 | 1 | 0.2 | | |
| 4 | 6.0 | 0.14 | ~0.20 | 0.005 | 2 | 1 | 0.2 | | |
| 6 | 6 | | 0.6 | 0.005 | 2 | | | | 366 |
| 4 | 5.0 | 1.14% | ~0.20 | 0.005 | 2 | | | | |
| 4 | 7.0 | 0.14% | ~0.20 | 0.005 | 2 | | | | |
| 5 | 6 | 0.14 | 1 | 0.005 | 2 | | | | 380 |
| 6 | 6 | | 1 | 0.005 | 2 | | | | 214 |
| 4 | 6.0 | 0.14% | ~0.20 | 0.005 | 2 | | | | |
| 5 | 6.0 | 0.14% | ~0.20 | 0.005 | 2 | | | | |
| 2 | 6.0 | 0.14% | ~0.20 | 0.005 | 2 | 1 | 0.2 | | |
| 2 | 6.1 | | 0.6 | 0.005 | 2 | 1 | 0.1 | 0.2 | 321 |
| 2 | 6.0 | 0.14% | ~0.20 | 0.005 | 2 | | | | |
| 2 | 6 | 0.14 | ~0.20 | 0.005 | 2 | | | | 276 |
| 2 | 6 | | 0.6 | 0.005 | 2 | | | | 312 |
| 1 | 6.0 | 0.14% | ~0.20 | 0.005 | 2 | | | | |
| 1 | 6.0 | 0.14% | ~0.20 | 0.005 | 2 | 1 | 0.2 | | |

| Days Dosing | Dose x per | MEAN [choroid] nM | SD [choroid] nM | Mean [retina] nM | SD [retina] nM | Mean [AH] nM | SD [AH] nM | [plasma] nM |
|---|---|---|---|---|---|---|---|---|
| 5 | 3x | 1520 | | | | 410 | | |
| 5 | 3x | 1190 | 551 | 210 | 85.2 | 195 | 190 | 13.3 |
| 5 | 3x | 1040 | 397 | 151 | 71.7 | 30.2 | 9.43 | 9.2 |
| 4 | 3x | 928 | | | | 68.4 | | 8.31 |
| 5 | 3x | 915 | 203 | 139 | 34.7 | 40.4 | 6.73 | 8.18 |
| 5 | 3x | 770 | 226 | 169 | 122 | 27.3 | 6.55 | 5.4 |
| 5 | 3x | 758 | | | | 34.9 | | |
| 4 | 3x | 701 | | | | 22 | | 5.68 |

TABLE 7-continued

PK results with topical ocular Compound-I in tromethamine-based suspension

| | | | | | | | | |
|---|---|---|---|---|---|---|---|---|
| 5 | 3x | 680 | 217 | 129 | 57.8 | 55.3 | 39.5 | 10.2 |
| 5 | 3x | 574 | 91.1 | 113 | 28.4 | 50.5 | 9.51 | 7.87 |
| 5 | 3x | 456 | 55.4 | 79.8 | 64 | 14.1 | 0.535 | 4.99 |
| 5 | 3x | 416 | | | | | | |
| 5 | 3x | 405 | 121 | 51.5 | 35.7 | 12.9 | 6.17 | 3.39 |
| 5 | 3x | 352 | | <LLoQ | | 19.9 | | 5.4 |
| 5 | 3x | 321 | | | | | | |
| 5 | 3x | 286 | 64.6 | 31.5 | 36.4 | 15.7 | 4.32 | 2.6 |
| 5 | 3x | 202 | 27.8 | 18.5 | 36.9 | 3.07 | 0.41 | 1.91 |

*CD: Compound 1

The present disclosure provides ocular bioavailability of Compound-I in the posterior segment upon administration of a tromethamine-based suspension. The ocular bioavailability of Compound-I in the posterior segment is directly proportional to the total amount of drug administered (insoluble plus soluble, see Table 7). Although the insoluble drug particulates are not readily available to anterior segment tissues; the inherent and unique physicochemical properties of Compound-I allow both insoluble and soluble components to gain entry to posterior segment tissues, such as the choroid and retina. Consequently, even higher drug concentrations than those achieved with Gel Drop formulations containing equivalent amounts of the active agent are achieved with the tromethamine-based suspension. Thus, tromethamine-based suspension provide: a) improved corneal tolerability and b) increased bioavailability to the posterior segment, particularly to the choroid, the primary target tissue for treating neovascular (wet) AMD.

Cyclodextrin-Based Solution

Cyclodextrins, which are cyclic oligosaccharides made up of six to eight dextrose units (α-, β-, and γ-CDs) joined through one to four bonds, are well-known for their ability to act as a solubilizing agent for relatively insoluble drugs. See Stella & He, Cyclodextrins, *Toxicol. Pathol.*, 36: 30-42 (2008).

In some embodiments, 2-hydroxypropyl-β-cyclodextrin (HP-β-CD, also known as KLEPTOSE® HPB) at equal to or more than 1:6 molar ratio or Sulfobutylether-β-cyclodextrin (SBE-β-CD, also known as CAPTISOL®) at β equal to or more than 1:2 ratio in the proposed clinical formulation, Compound-I or its free base Ophthalmic Solution, provide solubility that meets clinical dose strengths of 0.1-1.0% Compound-I.

In some embodiments, cyclodextrin-based solutions of Compound-I or its free base not only have improved solubility of the active agent into a uniform solution, but, upon topical ocular administration, also have a novel and previously unobserved characteristic of significantly increased therapeutic index of the active agent at the posterior segment of the eye. The solutions of Compound-I of the present disclosure reduce anterior segment exposure, thereby increase the concentration of the active in the solution and increase frequency of its delivery in order to maintain high posterior segment concentrations. Both of these beneficial characteristics are related to the known property of cyclodextrin to form hydrophilic complexes with hydrophobic drugs. See Stella & He, Cyclodextrins, *Toxicol. Pathol.*, 36: 30-42 (2008). When formulated with Compound-I or its free base, cyclodextrin formed a clear, colorless solution which exhibited water-like viscosity. Following topical ocular administration, Compound-I/cyclodextrin complex has the appearance of being pharmacologically inactive and metabolically inert. The Compound-I/cyclodextrin complex confers corneal tolerability until cyclodextrin spontaneously dissociates from the active agent, thus making available high concentration of Compound-I at its intended site of action in the posterior segment of the eye, e.g., choroid and retina.

In some embodiments, cyclodextrin-based solutions of Compound-I lower corneal exposures of Compound-I compared to Gel Drop formulations at similar drug concentrations. The use of cyclodextrin-based solutions of Compound-I provides about 10× reduction in corneal concentrations, as compared to dosing with equimolar formulations of the Gel Drop. In some embodiments, after 20-30 days of topical ocular dosing of about 0.2-2.0%, e.g., about 0.6%, Compound-I as a cyclodextrin-based solution, no untoward findings are attributed to test-article or vehicle. The present disclosure provides higher concentrations of Compound-I within the posterior segment target tissues, such as at the central choroid and the central retina, when cyclodextrin-based solution of Compound-I is topically applied. In some embodiments, the combined effects of decreasing corneal drug exposure so as to avoid poor ocular tolerability, while increasing posterior segment bioavailability so as to increase RTK inhibition, significantly increases the therapeutic index and corresponding benefit(s) to treated subjects.

The present disclosure provides expansion of therapeutic window for both suspension-based formulations (see Example 3) and the cyclodextrin formulations due to significantly reduced exposure (about 10-100× or 1-2 log reduction). The reduced exposure improves corneal safety/tolerability, which allows higher concentrations or frequency of dosing of Compound-I to be administered topically. The higher concentration enables Compound-I to achieve higher back of the eye target tissue concentration, which improves the therapeutic efficacy of Compound-I.

In some embodiments, topical ocular dosing of ophthalmic gel drops is associated with high corneal tissue exposure (≥100 uM) and corresponding untoward observations in the anterior segment, such as discomfort, corneal and conjunctival inflammation, corneal epithelial erosion and/or thinning and degeneration. In contrast, repeated topical ocular dosing of Compound-I ophthalmic solution produces corneal exposure that are roughly 5 to 10-fold lower than an equimolar dose of ophthalmic gel drops, and are free of untoward clinical or histopathologic findings. Topical ocular dosing with Compound-I ophthalmic solution also achieves equal or higher target therapeutic exposure in the central choroid in comparison to an equimolar dose of the ophthalmic gel drop. Overall, the combination of decreased corneal exposure and corresponding improved ocular tolerability, while simultaneously maintaining or promoting drug delivery to the posterior segment target tissues, along with improved physicochemical stability, provides greater benefit to subjects compared to the ophthalmic Gel Drop formulation.

1- to 5-Day PK Results with Topical Ocular Compound-I in Cyclodextrin-Based Solutions The present disclosure provides ocular pharmacokinetics of various formulations and dose regimens of Compound-I following topical ocular dose administration. Three dosage strengths in nine (9) different topical ocular formulations of Compound-I are used for dosing either once per day (q.d.) or twice per day (b.i.d.) for 1, 2, 3, 4, or 5 consecutive days. Subjects each receive about 30 µL bilateral topical ocular dose of one of three (3) Compound-I formulations, or vehicle formulation, using a positive displacement pipette.

The composition of each Compound-I formulation is described in Table 8A. All doses were administered within ±1 hour of the scheduled dose time. On day 1, Groups 1, 2, 4-6, 8, 10, 11, 13, 15, and 17 receive one dose (q.d.) for either one (1) or four (4) days. On days 1 through 4, Groups 3, 7, 9, 12, 14, and 16 receive b.i.d. dosing approximately 8 hours apart at 7:00 AM and 3:00 PM for four (4) days. Some subjects receive b.i.d dosing of vehicle only formulations for five (5) consecutive days.

In some embodiments, ocular sampling is performed at about 0.5, about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, or about 24 hours post-dose relative to the day 1 dose. Aqueous humor, cornea, central and peripheral retina, and central and peripheral choroid samples are collected to monitor effects of treatment. Aqueous humor, cornea, central retina, and central choroid samples are assayed.

Table 8A-C lists 1- to 5-day PK results with topical ocular Compound-I in Cyclodextrin-based solutions.

TABLE 8A

| | Ocular Formulations |
|---|---|
| Composition: | 0.3% Compound-I (3 mg/mL Compound-I) 0.05% Sodium Phosphate, monobasic, monohydrate, USP 2.0% glycerin, USP pH 6 |
| Physical Description: | Clear and colorless, extremely viscous |
| Composition: | 0.3% Compound-I (3 mg/mL Compound-I) 0.05% Sodium Phosphate, monobasic, monohydrate, USP 2.0% glycerin, USP pH 5.5 |
| Physical Description: | Clear and colorless |
| Composition: | 0.4% Compound-I (4 mg/mL Compound-I) 7% Hydroxypropyl-β-cyclodextrin (HPβCD), 0.7% Sodium Chloride, USP, 0.005% Benzalkonium chloride (BAK), NF pH 7.0 |
| Physical Description: | Clear and colorless, viscous |
| Composition: | 0.4% Compound-I (4 mg/mL Compound-I) 4% Hydroxypropyl-β-cyclodextrin (HPβCD), 0.7% Sodium chloride, USP, 0.005% Benzalkonium chloride (BAK), NF pH 7.0 |

TABLE 8A-continued

| | Ocular Formulations |
|---|---|
| Physical Description: | Clear and colorless, viscous |
| Composition: | 0.4% Compound-I (4 mg/mL Compound-I) 4% Hydroxypropyl-β-cyclodextrin (HPβCD), 0.7% Sodium Chloride, USP, 0.005% Benzalkonium chloride (BAK), NF pH 6 |
| Lot Number: | BCL532-052(5) ALG-001 |
| Physical Description: | Clear and colorless, extremely viscous |
| Composition: | 0.4% Compound-I (4 mg/mL, Compound-I) 7% Hydroxypropyl-β-cyclodextrin (HPβCD),1% Tromethamine, USP, 0.4% Sodium Chloride, USP, 0.005% Benzalkonium chloride (BAK), NF, pH 7.0 |
| Physical Description: | Clear and colorless |
| Composition: | 0.6% Compound-I (6 mg/mL Compound-I) 7% Hydroxypropyl-β-cyclodextrin (HPβCD), 0.7% Sodium Chloride, USP, 0.005% Benzalkonium chloride (BAK), NF pH 7.0 |
| Physical Description: | Clear and colorless, viscous |
| Composition: | 0.6% Compound-I (6 mg/mL Compound-I) 7% Hydroxypropyl-β-cyclodextrin (HPβCD), 0.7% Sodium Chloride, USP, 0.005% Benzalkonium chloride (BAK), NF, pH 6.0 |
| Physical Description: | Clear and colorless, viscous |
| Composition: | 0.4% Compound-I (4 mg/mL, Compound-I) 5% Cremophor RH40, 2,0% glycerin, USP, 0.005% Benzalkonium chloride (BAK), NF, pH 6.0 |
| Physical Description: | Clear and colorless |

Table 8B lists average Compound-I concentrations in aqueous humor, retina, choroid, and cornea (LLOQ: Lower Limit of Quantitation; the LLOQ is the lowest analyte concentration that can be quantified with acceptable precision and accuracy).

TABLE 8B

| | | Average Concentration of Compound-I (μM) | | | | | |
|---|---|---|---|---|---|---|---|
| Group | Time Point | Aqueous Humor | Central Retina | Peripheral Retina | Central Choroid | Peripheral Choroid | Cornea |
| 1 | 0.5 hr | 0.00162 | 0.0404 | 0.0291 | <LLOQ | <LLOQ | 57.6 |
|   | 1 hr | 0.00206 | <LLOQ | 0.0548 | <LLOQ | *0.0856 | 33.7 |
|   | 2 hr | 0.0103 | 0.0368 | 0.0779 | <LLOQ | 0.0575 | 44.5 |
|   | 8 hr | 0.0128 | 0.0340 | 0.0356 | <LLOQ | 0.134 | 29.2 |
|   | 24 hr | 0.00303 | <LLOQ | 0.0151 | <LLOQ | 0.0880 | 6.94 |
| 2 | 1 hr | 0.00996 | 0.0363 | 0.0961 | *0.207 | 0.737 | 112 |
|   | 8 hr | 0.0165 | 0.0380 | 0.0508 | *0.237 | 0.687 | 32.7 |
|   | 24 hr | 0.00336 | <LLOQ | 0.380 | *0.205 | 1.14 | 29.7 |
| 3 | 1 hr | 0.0142 | 0.0407 | 0.108 | 0.255 | 0.765 | 151 |
|   | 24 hr | 0.00774 | 0.0292 | 0.0597 | 0.283 | 0.892 | 82.1 |
| 4 | 1 hr | 0.00996 | 0.0431 | 0.0883 | 0.196 | 0.629 | 78.7 |
| 5 | 0.5 hr | <LLOQ | <LLOQ | 0.0227 | <LLOQ | <LLOQ | 21.0 |
|   | 1 hr | 0.00108 | 0.0211 | 0.0253 | <LLOQ | 0.0473 | 16.9 |
|   | 2 hr | 0.00862 | 0.0354 | 0.0253 | <LLOQ | 0.0509 | 28.1 |
|   | 4 hr | 0.00911 | 0.0299 | 0.0312 | <LLOQ | 0.0775 | 14.1 |
|   | 8 hr | 0.00667 | 0.0304 | 0.0333 | <LLOQ | 0.0874 | 7.74 |
|   | 24 hr | 0.00228 | <LLOQ | *0.0103 | <LLOQ | 0.116 | 2.43 |
| 6 | 1 hr | 0.00323 | 0.0463 | 0.0634 | 0.319 | 0.311 | 21.8 |
|   | 8 hr | 0.00742 | 0.0537 | 0.0349 | <LLOQ | 0.257 | 9.10 |
|   | 24 hr | 0.00122 | 0.0241 | 0.0533 | <LLOQ | 0.343 | 2.33 |
| 7 | 1 hr | 0.00648 | 0.0469 | 0.0819 | 0.514 | 0.744 | 35.3 |
|   | 24 hr | 0.00260 | 0.0313 | 0.0293 | 0.439 | 0.653 | 13.0 |
| 8 | 1 hr | 0.00978 | 0.0490 | 0.0497 | 0.367 | 0.797 | 63.2 |
|   | 24 hr | 0.00483 | 0.0193 | 0.0177 | 0.218 | 1.20 | 37.4 |
| 9 | 1 hr | 0.0246 | 0.0633 | N/A | 0.456 | N/A | 237 |
| 10 | 1 hr | 0.00867 | 0.0667 | N/A | 0.251 | N/A | 93.9 |

AH LLOQ = 0.000903 μM
Central Retina LLOQ = 0.0181 μM
Peripheral Retina LLOQ = 0.00873 μM (Grps 1-8); LLOQ = 0.00898 μM (Grps 12-16)
Central Choroid LLOQ = 0.175 μM
Peripheral Choroid LLOQ = 0.0349 μM. (Grps 1-8): LLOQ = 0.0359 μM (Grp 12-16)
Cornea LLOQ = 0.0181 μM (Grp 1-5); LLOQ = 0.0453 μM (Grp 6-8, 10-13, 15, 16A17), LLOQ = 0.0873 μM (Grp 4, 9, 16B)
N/A = Not Applicable; Samples not assayed per study protocol.
*Average based on n = 1.

Table 8C lists the summary of average ocular tissue concentrations of Compound-I in aqueous humor, central and peripheral retina, central and peripheral choroid, and cornea for Groups 1 through 10. Any values <LLOQ were excluded from statistical calculations. When all values are <LLOQ for a given time point, <LLOQ are reported as the average.

5-Day PK Results with Topical Ocular Compound-I in Cyclodextrin-Based Solutions

The present disclosure provides ocular pharmacokinetics of various dose regimens of topical ocular solutions of Compound-I containing hydroxypropyl-β-cyclodextrin ("HDβCD") following ocular dose administration. Different topical ocular solutions of Compound-I are administered either once per day (q.d.) or twice per day (b.i.d.) for either

TABLE 8C

| | | Average Concentration of Compound-I (μM) | | | | | |
|---|---|---|---|---|---|---|---|
| Group | Time Point | Aqueous Humor | Central Retina | Peripheral Retina | Central Choroid | Peripheral Choroid | Cornea |
| 11 | 1 hr | 0.00284 | 0.0397 | N/A | 0.193 | N/A | 20.7 |
|    | 24 hr | *0.00205 | *0.0185 | N/A | *0.179 | N/A | 0.487 |
| 12 | 1 hr | 0.00651 | 0.0521 | 0.0842 | 0.528 | 0.560 | 27.4 |
| 13 | 1 hr | 0.0102 | 0.0934 | N/A | 0.372 | N/A | 123 |
|    | 24 hr | 0.00518 | 0.0246 | N/A | 0.319 | N/A | 39.1 |
| 14 | 1 hr | 0.0209 | 0.0817 | 0.151 | 7.19 | 1.00 | 236 |
| 15 | 1 hr | 0.0114 | 0.0527 | N/A | 0.319 | N/A | 82.9 |
| 16 | 1 hr | 0.0179 | 0.0480 | 0.169 | 0.495 | 0.868 | 169 |
| 17 | 1 hr | 0.00445 | 0.0468 | N/A | 0.297 | N/A | 32.0 |

AH LLOQ = 0.000903 μM
Central Retina LLOQ = 0.0181 μM
Peripheral Retina LLOQ = 0.00873 μM (Grps 1-8); LLOQ = 0.00898 μM (Grps 12-16)
Central Choroid LLOQ = 0.175 μM
Peripheral Choroid LLOQ = 0.0349 μM. (Grps 1-8): LLOQ = 0.0359 μM (Grp 12-16)
Cornea LLOQ = 0.0181 μM (Grp 1-5); LLOQ = 0.0453 μM (Grp 6-8, 10-13, 15, 16A17), LLOQ = 0.0873 μM (Grp 4, 9, 16B)
N/A = Not Applicable; Samples not assayed per study protocol.
*Average based on n = 1.

4 or 5 consecutive days. Subjects each receive a 30 μL bilateral topical ocular dose of one of four Compound-I dosage strengths.

All doses were administered with ±1 hour of the scheduled dose time, except some subjects receiving on day 1. Ocular sampling after administration of Compound-I is performed one hour following the first daily dose on day 5 for subjects, except in a few, where ocular sampling is performed 24 hours after the first daily dose on day 4.

Aqueous humor, cornea, central and peripheral retina, and central and peripheral choroid samples are collected. Cornea, central retina, and central choroid samples are assayed; aqueous humor, peripheral retina, and peripheral choroid samples are not assayed.

Table 9 (A-B) lists 5-day PK results with topical ocular Compound-I in cyclodextrin-based solutions.

TABLE 9A

Ocular Formulations

| Formulation 1 (A) | Composition: | 0.4% Compound-I (as free base 7.15% Hydroxypropyl-β-cyclodextrin 0.7% Sodium chloride pH 6.5 |
| --- | --- | --- |
| | Physical Description: | Clear and colorless |
| Formulation 2 (B) | Composition: | 0.1% Compound-I (as free base 1.79% Hydroxypropyl-β-cyclodextrin 0.85% Sodium chloride pH 6.5 |
| | Physical Description: | Clear and colorless |
| Formulation 3 (C) | Composition: | 0.2% Compound-I (as free base) 3.57% Hydroxypropyl-β-cyclodextrin 0.8% Sodium chloride pH 6.5 |
| | Physical Description: | Clear and colorless |
| Formulation 4 (D) | Composition: | 0.6% Compound-I (as free base) 10.72% Hydroxypropyl-β-cyclodextrin 0.6% Sodium chloride pH 6.5 |
| | Physical Description: | Clear and colorless |
| Formulation 5 (E) | Composition: | 0.4% Compound-I (as free base) 8.41% Hydroxypropyl-β-cyclodextrin 0.65% Sodium chloride pH 6.5 |
| | Physical Description: | Clear and colorless |
| Formulation 6 (F) | Composition: | 0.4% Compound-I (as free base 10.51% Hydroxypropyl-β-cyclodextrin 0.65% Sodium chloride pH 6.5 |
| | Physical Description: | Clear and colorless |
| Formulation 7 (G) | Composition: | 0.4% Compound-I (as free base 10.51% Hydroxypropyl-β-cyclodextrin 0.15% Sodium chloride 1.0% Tromethamine (Tris) pH 6.5 |
| | Physical Description: | Clear and colorless |
| Formulation 8 (H) | Composition: | 0.1% Compound-I (as free base 2.63% Hydroxypropyl-β-cyclodextrin 0.8% Sodium chloride pH 6.5 |
| | Physical Description: | Clear and colorless |
| Formulation 9 (I) | Composition: | 0.6% Compound-I (as free base 15.77% Hydroxypropyl-β-cyclodextrin 0.37% Sodium chloride pH 6.5 |
| | Physical Description: | Clear and colorless |

Table 9B lists a summary of average ocular tissue concentrations of Compound-I in central retina, central choroid, and cornea. Any values <LLOQ were excluded from statistical calculations. When all values were <LLOQ for a given time point, <LLOQ was reported as the average.

TABLE 9B

Average Compound-I concentrations in retina, choroid, and cornea.

| | | Average Concentration (μM) | | |
| --- | --- | --- | --- | --- |
| Group | Time Point | Central Retina | Central Choroid | Cornea |
| 1 | 1 hr | 0.0670 | 0.308 | 35.1 |
| 2 | 1 hr | 0.0636 | 0.329 | 21.8 |
| 3 | 1 hr | 0.0579 | 0.313 | 18.2 |
| 4 | 1 hr | 0.0481 | 0.203 | 12.9 |
| 5a | 1 hr | 0.0403 | *0.199 | 12.8 |
| 5b | 24 hr | <LLOQ | 0.194 | 0.772 |
| 6a | 1 hr | 0.0469 | 0.309 | 10.6 |
| 6b | 24 hr | <LLOQ | *0.218 | 0.371 |
| 7 | 1 hr | 0.0332 | <LLOQ | 7.60 |
| 8 | 1 hr | 0.0376 | *0.210 | 5.41 |
| 9 | 1 hr | 0.0261 | *0.287 | 8.53 |
| 10 | 1 hr | 0.0534 | 0.264 | 16.7 |
| 11 | 1 hr | 0.0418 | 0.371 | 29.6 |
| 12 | 1 hr | 0.0464 | 0.210 | 16.3 |

Central Retina LLOQ = 0.0218 μM
Central Choroid LLOQ = 0.174 μM
Cornea LLOQ = 0.0174 μM
*Average based on n = 1

Concentrations of Compound-I (in μM) in Various Ocular Fluids and Tissues

In some embodiments, concentration of the active agent in various tissues and fluids of the eye is measured upon topical ocular administration of a solution of about 0.4% (about 4 mg/mL) Compound-I and cyclodextrin. Average concentration of Compound-I is measured in the central choroid, central retina, aqueous humor, and cornea. Compound-I is in a solution (0.4% or 4 mg/mL) with 8.41% KLEPTOSE® and 0.142% phosphate buffer; 8.9% KLEPTOSE® HPB and 0.142% phosphate; 4.88% CAPTISOL® and 0.142% phosphate; or 4.88% CAPTISOL® and 0.122% phosphate. See Table 10A-B.

In some embodiments, upon topical ocular administration of a solution of about 0.4% (about 4 mg/mL) Compound-I and cyclodextrin, the central choroid concentration of Compound-I is between about 0.2 μM and about 0.8 μM. The central retina concentration of Compound-I is between about 0.05 μM-about 0.15 μM. In some embodiments, upon topical ocular administration of a solution of about 0.4% (about 4 mg/mL) Compound-I and cyclodextrin, the aqueous humor concentration of Compound-I is between about 0.003 μM-about 0.008 μM. And the corneal concentration of Compound-I is about 6.0 μM-about 40 μM. KLEPTOSE® HPB or CAPTISOL® is used in the solution of Compound-I administered topically to the eye.

In some embodiments, mean Compound-I ocular tissue concentrations following twice daily topical dosing with 0.3% Compound-I ophthalmic gel drop formulations with and without benzylalkonium chloride is highest in the cornea with between about 200 μM-about 350 μM in the cornea, between about 2.0 μM-about 5.0 in the peripheral choroid, between about 0.2 μM-about 0.7 μM in the central choroid, between about 0.05 μM-about 0.5 μM in the peripheral retina, and between about 0.01 μM-about 0.05 μM in the aqueous humor.

In some embodiments, Tris-based suspension formulations of Compound-I is well tolerated, without any corneal findings, and only with a few sporadic incidences of mild conjunctivitis. In some embodiments, mean Compound-I ocular tissue concentrations, assessed at 1 hour±15 minutes after the first daily topical ocular dose on day 30 for the twice daily topical dosing with 0.3% Compound-I Tris-based suspensions with and without benzylalkonium chloride, are highest in the cornea, for example, between about 2.00 µM-about 4.0 µM. The peripheral choroid concentration from the same dose is between about 0.7 µM-about 1.5 µM: the central choroid concentration is between about 0.3 µM-about 0.4 µM; the peripheral retina concentration is between about 0.08 µM-about 0.09 µM); central retina concentration is between about 0.04 µM-about 0.07 µM; and aqueous humor concentration is about 0.001 µM-about 0.002 µM.

The present disclosure provides Cyclodextrin-based solutions (e.g., solutions comprising hydroxypropyl-beta-cyclodextrin (HP-β-CD, KLEPTOSE® HPB)) of Compound-I that were well tolerated when administered topically for up to 30 days, twice daily at about 0.1% Compound-I (in a solution with about 2.0%-about 2.5% HP-β-CD), twice daily at about 0.2% Compound-I (in a solution with about 4.0%-about 4.5% HP-β-CD), once or twice daily at about 0.4% w/v of a cyclodextrin-based solution or a Tris-based suspension of Compound-I is well tolerated in subjects. The present disclosure provides highest central choroid concentrations of Compound-I using Cyclodextrin-based solutions compared to equimolar doses of the gels and/or Tris-based formulations.

TABLE 10A

Average concentration of Compound-I in µM in various ocular fluids and tissues

| Group | Central Choroid | Central Retina | Aqueous Humor | Cornea |
|---|---|---|---|---|
| 8 | 0.769 | 0.124 | 0.00656 | 12.3 |
| 9 | 0.259 | 0.0741 | 0.00313 | 8.05 |
| 10 | 0.212 | 0.0531 | 0.00184 | 6.49 |
| 11 | 0.345 | 0.101 | 0.00403 | 30.0 |

Values <LLOQ were excluded from statistical calculations.
Choroid LLOQ = 0.184 µM
Retina LLOQ = 0.0229 µM
AH LLOQ = 0.000918 µM
Cornea LLOQ = 0.0918 µM

TABLE 10B

Study Design

| Group | Total Daily Dose* (mg/day) | Conc.* (% w/v) | Dose Volume (µL/dose) | Number of Doses per Day | Total Dose Volume (µL/day) | Number of Male Animals |
|---|---|---|---|---|---|---|
| Group 8. Compound-I in 8.41% KLEPTOSE® HPB**, 0.142% phosphate | 0.48 | 0.4 | 30/eye | 2 | 120 | 2 |
| Group 9. Compound-I in 8.90% KLEPTOSE® HPB, 0.142% phosphate | 0.48 | 0.4 | 30/eye | 2 | 120 | 2 |
| Group 10. Compound-I in 4.88% CAPTISOL®***, 0.142% phosphate | 0.48 | 0.4 | 30/eye | 2 | 120 | 2 |
| Group 11. Compound-I in 4.88% CAPTISOL®, 0.122% phosphate | 048 | 0.4 | 30/eye | 2 | 120 | 2 |

*Total daily dose and concentration are expressed as free base equivalent of Compound-I (Formula II).
**Hydroxypropyl-β-cyclodextrin (HPβCD) from Roquette.
***CAPTISOL® is a polyanionic β-cyclodextrin derivative with a sodium sulfonate salt separated from the lipophilic cavity by a butyl ether spacer group, or sulfobutylether (SBE).

Compound-I (in a solution with about 8.0%-about 8.5% HP-β-CD), and once or twice daily at about 0.6% Compound-I (in solution with up to about 14% HP-β-CD) in subjects. Moreover, in additional embodiments, cyclodextrin-based solutions of about 0.4% w/v Compound-I in KLEPTOSE® HPB, KLEPTOSE® HP, or CAPTISOL® are well-tolerated when dosed twice daily for up to 24 days.

The present disclosure provides dose-limiting corneal toxicity observed with Compound-I ophthalmic Gel Drop formulations. In some embodiments, ophthalmic Gel Drop renders about five-fold to about fifteen-fold higher corneal concentrations of Compound-I compared to cyclodextrin based solution, and about fifty-fold to about hundred-fold higher corneal concentrations of Compound-I compared to Tris-based suspensions. Compound-I Tris-based suspensions and cyclodextrin-based solutions of the present disclosure are well tolerated with no evidence of overt ocular toxicity. In some embodiments, once or twice daily administration for at least 30 days of about 0.005% to about 5.0%

Table 11 shows the corneal and central choroidal concentrations of Compound-I formulations.

TABLE 11

Phase I Protocol for Dose-Escalation Study in Patients with Neovascular AMD

| Compound-I w/v % | Formulation Type | Dosing Frequency & Duration | Cornea [Compound I] (µM) | Central Choroid [Compound I] (µM) |
|---|---|---|---|---|
| 0.3% | Ophthalmic Gel Drop | Twice Daily 29 days | 236.00 | 0.340 |
| 0.3% | Tris Suspension | Twice Daily 30 days | 2.69 | 0.319 |
| 0.4% | Ophthalmic Solution (CAPTISOL®) | Twice Daily 24 days | 6.49 | 0.212 |

TABLE 11-continued

Phase I Protocol for Dose-Escalation Study in Patients with Neovascular AMD

| Compound-I w/v % | Formulation Type | Dosing Frequency & Duration | Cornea [Compound I] (µM) | Central Choroid [Compound I] (µM) |
|---|---|---|---|---|
| 0.4% | Ophthalmic Solution (KLEPTOSE ®, HP) | Twice Daily 24 days | 8.05 | 0.259 |
| 0.4% | Ophthalmic Solution (KLEPTOSE ® HPB) | Twice Daily 24 days | 12.30 | 0.769 |

Phase I Protocol for Dose-Escalation Study in Patients with Neovascular AMD

The present disclosure provides a Phase I study involving a twelve-week, open-label, dose-escalating, multi-center trial to evaluate the safety, tolerability, and pharmacokinetics following topical ocular administration of Compound-I in patients with neovascular age-related macular degeneration (AMD). Up to 60 patients total are treated one to two times daily with topical ocular dosing of Compound-I ophthalmic solution for three months, where three dose-escalating monotherapy arms and one adjunct therapy arm using a single intravitreal injection of LUCENTIS® plus the maximally-tolerated monotherapy dose are planned (15 patients per treatment arm). Patients that meet pre-specified vision and CNV lesion criteria confirmed by an independent reading center are allowed to simultaneously discontinue topical ocular dosing and receive treatment with standard-of-care.

The present disclosure provides 3 dosage strengths, ranging from 0.1% to 1.0% (w/v) (as Compound-I) ophthalmic solution for clinical studies. The strengths are about 0.1%, about 0.3%, about 0.6%, and about 1.0% (w/v) Compound-I HCl.

Formulation Preparation

Non-limiting examples of formulations of the present disclosure are outlined in Table 12.

TABLE 12

Overview of product compositions tested in product screening studies

| Cyclodextrin Type and Ratio Range[a] | Cyclodextrin Conc. Range | Compound-I Conc. | pH | Buffer type and level |
|---|---|---|---|---|
| HPβCD[b] 1:4, 1:8, 1:10, 1:12 | 6.3 to 18.9% | 0.6% | 7 | None and Tris |
| HPβCD 1:6, 1:8, 1:10 | 1.58 to 15.6% | 0.1 and 0.6% | 6 | None and Tris |
| HPβCD 1:6, 110 | 1.58 to 2.63% | 0.1% | 6.5, 7 | None and Tris |
| SBECD 1:2, 1:3, 1:4, 1:6, 1:8,1:10 | 0.81 to 19.5% | 0.1 and 0.6% | 6 | Phosphate |
| SBECD[c] | 1:3 | 0.1, 0.4% | 5.5, 6.5 | Phosphate, Tris |
| HPβCD | 1:8 | 0.1, 0.4% | 5.5, 6.5 | Phosphate, Tris |

[a]Molar ratio of Compound-I : cyclodextrin.
[b]KLEPTOSE ® HPB
[c]CAPTISOL ®

Doses of Treatment

The formulation of the current invention is effective in treating or preventing (i.e., regression) choroidal and retinal neovascularization (NV) in the eye of a mammalian subject. The Compound-I of the current invention, at a specific dose, inhibits a receptor tyrosine kinase. In some embodiments, the Compound-I formulation, at a specific dose, inhibits receptor tyrosine kinase including, VEGFR, FGFRs, Tie2, and EphB-4. The inhibition of several RTKs by the formulation of the current invention, at a specific dose, simultaneous and has a synergistic effect, and is effective in the treatment or regression of NV in the posterior segment of the eye.

In further embodiment, the formulation of the current invention is effective in treating NV when administered one, two, three, and four times daily by topical ocular delivery of about 0.005%-about 5.0% (about 0.05-about 50 mg/mL) of Compound-I. The formulation of Compound-I or its free base (Formula II), for the treatment or regression of NV, is a solution comprising cyclodextrin or in a suspension comprising Tris. The solution or suspension when delivered to a subject exposed to atmospheric oxygen to induce oxygen induced retinopathy (OIR) or NV, for example, is able to effectively reduce the mean area of pre-retinal NV per retina. The prevention or treatment of NV by Compound-I formulation and/or suspension is achieved via inhibition of several receptor tyrosine kinases (RTKs), including VEGFR-2.

Any of the disclosed diseases or conditions described herein can be treated or prevented by achieving target tissue concentration of from about 200 nM-about 2 µM of the disclosed compounds or pharmaceutically acceptable salts, formulation and/or suspension thereof. One embodiment of this invention relates to a method for treating pathologic angiogenesis in the posterior segment of the eye, achieving target tissue concentration of about of about 200 nM-about 2 µM of the disclosed compounds or pharmaceutically acceptable salts, and/or formulation thereof. Another iteration of this embodiment relates to achieving target tissue concentration of about 300 nM-about 2 µM of one or more of the disclosed compounds or pharmaceutically acceptable salts, and/or formulation thereof.

In an embodiment of the current invention about 0.2-about 1.0% (about 2-about 10 mg/mL) of Compound-I formulated as a solution or suspension, upon administration, may effectively inhibit VEGFR-2 kinase function and provide substantial blockade of a set of proangiogenic growth factor receptors, including FGFRs1-3, Tie-2, and EphB-4. The 2-10 mg/mL concentration of the Compound-I in the formulation provides effective pharmacologically effective concentrations of drug to the central choroid and retina following 1-5 days of topical ocular delivery.

In some embodiments, the exposure time of Compound-I is between 1 and 90 days. In some embodiments, the dosage regimen involves several courses of topical ocular administration of a formulation comprising Compound-I to a subject for between 1 and 90 days. For example, the dosage regimen involves once daily, twice daily, three times daily or four times daily administration of the formulation for between 1 and 90 days. For example, the dosage regimen involves once, twice, three times, or four times administration of the formulation on every other day (i.e., on day 1, 3, 5, 7 etc.) for up to 90 days. For example, the dosage regimen involves administering once on day 1, once or twice on day 2-day 90. For example, the dosage regimen involves administering once, twice, three times, or four times on day 1, followed by once daily for 2-90 days. For example, the dosage regimen involves administering once, twice, three times, four times on day 1, followed by once, twice, three times, or four times on every other day (i.e., on day 1, 3, 5, 7 etc.) for up to 90 days. For example, one dosage regimen involves once per day or twice per day for 1, 2, 3, 4, or 5 consecutive days. For twice or three daily dosage regimen, subjects receive topical ocular dose of a Compound-I formulation on days 1 and 4 approximately about 4, 6, or 8 hours apart. In another embodiment, subjects receive topical ocular doses of a Compound-I formulation approximately about 4, 6, or 8 hours apart for four consecutive days. In some embodiments, subjects receive one or two doses of topical ocular dose of Compound-I formulation per day for 5 consecutive days. In yet other embodiments, subjects receive one or two doses of topical ocular dose of Compound-I formulation for 5-90 consecutive days. In some embodiments, subjects receive one or two doses of topical ocular dose of Compound-I formulation for at least 25 consecutive days. In one embodiment, subjects receive one or two topical ocular doses for at least 90 consecutive days or more.

In some embodiments, the present disclosure provides a formulation of Compound-I or its free base administered topically to the anterior segment of the eye of the subject to treat AMD, pathologic CNV, and/or pathologic NV. For example, the formulation is administered to the eye of a subject 1, 2, 3, or 4 times daily. In specific embodiments, the formulation is administered to the eye of a subject 2 or 3 times daily. For example, the formulation is administered to one eye or both eyes of a subject. For example, about 1 mg/ml of an active agent comprising formulation of the current disclosure is administered twice a day (BID) to one eye or both eyes of a subject. In some embodiments, about 2 mg/mL BID, about 3 mg/mL once a day (QD) or BID, about 4 mg/mL QD or BID, about 5 mg/mL QD or BID, or about 6 mg/mL QD or BID of is administered to one eye or both eyes of a subject.

For example, a formulation comprising about 2 mg/mL BID of Compound-I is administered to one eye or both eyes of a subject for between 1 and 90 days. In some embodiments a formulation comprising about 3 mg/mL BID of Compound-I is administered to one eye or both eyes of a subject for between 1 and 90 days. In some embodiments a formulation comprising about 3 mg/mL QD of Compound-I is administered to one eye or both eyes of a subject for between 1 and 90 days. In some embodiments a formulation comprising about 4 mg/mL BID of Compound-I is administered to one eye or both eyes of a subject for between 1 and 90 days. In some embodiments a formulation comprising about 4 mg/mL QD of Compound-I is administered to one eye or both eyes of a subject for between 1 and 90 days. In some embodiments a formulation comprising about 5 mg/mL BID of Compound-I is administered to one eye or both eyes of a subject for between 1 and 90 days. In some embodiments a formulation comprising about 5 mg/mL QD of Compound-I is administered to one eye or both eyes of a subject for between 1 and 90 days. In some embodiments a formulation comprising about 6 mg/mL BID of Compound-I is administered to one eye or both eyes of a subject for between 1 and 90 days. In some embodiments a formulation comprising about 6 mg/mL QD of Compound-I is administered to one eye or both eyes of a subject for between 1 and 90 days. The dosage regimen for between 1 and 90 days may be any of the regimens involving consecutive or alternate days described in the paragraph above.

The present disclosure provides formulations as shown in Table 13 for administering to one eye or both eyes of a subject.

TABLE 13

| Dose/Day | Formula II (%) | Compound-I (%) | Formula II/Compound-I:CD | KLEPTOSE ® HPB (%) | 10 mM Phosphate (%) | Sodium Chloride (%)* | pH |
|---|---|---|---|---|---|---|---|
| QD | 0.40 | 0.427 | 1:8 | 8.411 | 0.142 | QS to about 285 mOsm | 6 |
| QD | 0.60 | 0.641 | 1:8 | 12.626 | 0.142 | QS to about 285 mOsm | 6 |
| BID | 0.10 | 0.107 | 1:8 | 2.103 | 0.142 | QS to about 285 mOsm | 6 |
| BID | 0.20 | 0.214 | 1:8 | 4.205 | 0.142 | QS to about 285 mOsm | 6 |
| BID | 0.30 | 0.321 | 1:8 | 6.308 | 0.142 | QS to about 285 mOsm | 6 |
| BID | 0.40 | 0.427 | 1:8 | 8.411 | 0.142 | QS to about 285 mOsm | 6 |

*QS = quantity sufficient for achieving the osmolality

In some embodiments, the formulation of Formula (II) or Compound-I is administered to one eye or both eyes of a subject. For example, about 0.2%-about 0.6% (w/v) of the compound of Formula (II) or about 0.1%-0.7% (w/v) of Compound-I comprising formulation of the current disclosure is administered once a day (QD) or twice a day (BID) to one eye or both eyes of a subject for between 1 and 90 days. In some embodiments, Formula (II) compound or Compound-I is complexed with a complexing agent, e.g., cyclodextrin (e.g., KLEPTOSE® HPB (%)) in ratio of about 1:8, in which about 2%-13% (w/v) cyclodextrin (e.g., KLEPTOSE® HPB (%)) is added to the formulation. The formulation further comprises about 0.1%-about 0.2% buffer, e.g., 10 mM phosphate buffer. The desired osmolality of the formulation is about 200-about 300 mOsm, achieved by adding quantity sufficient to achieve the osmolality with a salt, e.g., sodium chloride. The pH of the formulation is about 6.0 at or under about 40° C. The dosage regimen for between 1 and 90 days may be any of the regimens involving consecutive or alternate days described in the paragraph above.

The methods of the present disclosure are combined with the standard of care, including but not limited to laser treatment and treatment with injectable anti-neovascular agents.

Indications and Methods of Treatment

Disclosed are methods for the treatment of diseases or conditions of the eye. The disclosed methods relate to treating, preventing, or controlling ocular neovascularization (NV), or treating a disease or condition that is related to the onset of NV by administering to a subject one or more of the disclosed compounds, and formulations thereof.

One aspect of the disclosed method relates to treating or preventing NV by administering to a subject an effective amount of one or more of the disclosed compounds or pharmaceutically acceptable salts, and/or formulations thereof. One embodiment of this aspect relates to a method for treating NV by administering to a subject a composition of: a) an effective amount of one or more of the disclosed compounds or pharmaceutically acceptable salts, and/or formulations thereof, and optionally b) one or more carriers or compatible excipients.

The disclosed methods relate to preventing or controlling pathologic ocular neovascularization (NV), or treating a disease or condition that is related to the onset of NV by administering to a subject one or more of the disclosed compounds, and formulations thereof.

The current embodiments provide use of a formulation of Compound-I or its free base (formula II) for the manufacture of a medicament for treating a subject with a posterior segment disease vasculopathic or inflammatory disease of the eye. These include for example, diabetic retinopathy (including background diabetic retinopathy, proliferative diabetic retinopathy and diabetic macular edema); age-related macular degeneration (AMD) (including neovascular (wet/exudative) AMD, dry AMD, and Geographic Atrophy); pathologic choroidal neovascularization (CNV) from any mechanism (i.e. high myopia, trauma, sickle cell disease; ocular histoplasmosis, angioid streaks, traumatic choroidal rupture, drusen of the optic nerve, and some retinal dystrophies); pathologic retinal neovascularization from any mechanism (i.e., sickle cell retinopathy, Eales disease, ocular ischemic syndrome, carotid cavernous fistula, familial exudative vitreoretinopathy, hyperviscosity syndrome, idiopathic occlusive arteriolitis; birdshot retinochoroidopathy, retinal vasculitis, sarcoidosis, or toxoplasmosis); uveitis; retinal vein occlusion (central or branch); ocular trauma; surgery induced edema; surgery induced neovascularization; cystoid macular edema: ocular ischemia; retinopathy of prematurity; Coat's disease; sickle cell retinopathy and/or neovascular glaucoma.

In one aspect of the current invention the formulation is used in the treatment of age-related macular degeneration (AMD) (including neovascular (wet/exudative) AMD, dry AMD, and Geographic Atrophy). The solutions or suspensions are used in the treatment of neovascular (exudative or wet) AMD. In another embodiment, the solutions or suspensions are used to treat dry AMD. In yet another embodiment, the solutions or suspensions are used to treat Geographic Atrophy.

The formulation of the current invention prevents, delays, or treats the onset of pathologic choroidal neovascularization (CNV) from any mechanism (i.e. high myopia, trauma, sickle cell disease; ocular histoplasmosis, angioid streaks, traumatic choroidal rupture, drusen of the optic nerve, and some retinal dystrophies) in subjects.

The formulation of the current invention delays onset, prevents progression, or treats formation of pathological choroidal neovascularization (CNV) below the neurosensory retina. The formulation of the current invention is effective in treating CNV.

One aspect of this method relates to treating or preventing ocular neovascularization by administering to a subject an effective amount of one or more of the disclosed compounds or pharmaceutically acceptable salts thereof. One embodiment of this aspect relates to a method for treating ocular edema and neovascularization by administering to a subject a composition of: a) an effective amount of one or more of the disclosed compounds or pharmaceutically acceptable salts, and/or formulations thereof, and optionally b) one or more carriers or compatible excipients.

The disclosed methods also relate to preventing or controlling ocular edema or treating a disease or condition that is related to the onset of ocular edema by administering to a subject one or more or the disclosed compounds.

One aspect of this method relates to treating or preventing ocular edema by administering to a subject an effective amount of one or more of the disclosed compounds or pharmaceutically acceptable salts thereof. One embodiment of this aspect relates to a method for treating ocular edema by administering to a subject a composition of: a) an effective amount of one or more of the disclosed compounds or pharmaceutically acceptable salts and/or formulations thereof, and optionally b) one or more carriers or compatible excipients.

Another disclosed method relates to preventing or controlling retinal edema or retinal neovascularization or treating a disease or condition that is related to the onset of retinal edema or retinal neovascularization by administering to a subject one or more or the disclosed compounds. One aspect of this method relates to treating or preventing retinal edema or retinal neovascularization by administering to a subject an effective amount of one or more of the disclosed compounds or pharmaceutically acceptable salts thereof. One embodiment of this aspect relates to a method for treating retinal edema or retinal neovascularization by administering to a subject a composition of: a) an effective amount of one or more of the disclosed compounds or pharmaceutically acceptable salts, and/or formulations thereof, and optionally b) one or more carriers or compatible excipients.

Another embodiment of this aspect relates to a method for delaying or preventing progression of non-proliferative retinopathy to proliferative retinopathy by administering to a subject a composition of: a) an effective amount of one or more of the disclosed compounds or pharmaceutically acceptable salts, and/or formulations thereof, and optionally b) one or more carriers or compatible excipients.

One aspect of the disclosed methods relates to diseases that are a direct or indirect result of diabetes, inter alia, diabetic macular edema and diabetic retinopathy. The ocular vasculature of the diabetic becomes unstable over time leading to conditions such as non-proliferative retinopathy, macular edema, and proliferative retinopathy. As fluid leaks into the center of the macula, the part of the eye where sharp, straight-ahead vision occurs, the buildup of fluid and the associated protein begin to deposit on or under the macula. This results in swelling that causes the subject's central vision to gradually become distorted. This condition is referred to as "macular edema." Another condition that may occur is non-proliferative retinopathy in which vascular changes, such as microaneurysms, outside the macular region of the eye may be observed. During proliferative DR, pathologic new blood vessels grow in and up from the retina into to the vitreous body, where these abnormal vessels may alter retinal morphology in the macula, and/or hemorrhage into the vitreous and obscure the visual axis.

A further disclosed method relates to treating, preventing or controlling diabetic retinopathy or treating a disease or condition that is related to the onset of diabetic retinopathy by administering to a subject one or more or the disclosed compounds.

One aspect of the disclosed method relates to treating or preventing diabetic retinopathy by administering to a subject an effective amount of one or more of the disclosed compounds or pharmaceutically acceptable salts thereof. One embodiment of this aspect relates to a method for treating diabetic retinopathy by administering to a subject a composition of: a) an effective amount of one or more of the disclosed compounds or pharmaceutically acceptable salts, and/or formulations thereof, and optionally b) one or more carriers or compatible excipients.

Diabetic proliferative retinopathy is characterized by neovascularization. The new blood vessels are fragile and are susceptible to bleeding. The result is scarring of the retina, as well as occlusion or total blockage of the light pathway through the eye due to the abnormal formation of new blood vessels. Typically subjects having diabetic macular edema are suffering from the non-proliferative stage of diabetic retinopathy; however, it is not uncommon for subjects to only begin manifesting macular edema at the onset of the proliferative stage.

Yet a further disclosed method relates to preventing or controlling diabetic macular edema or treating a disease or condition that is related to the onset of diabetic macular edema by administering to a subject one or more or the disclosed compounds.

One aspect of this method relates to treating or preventing diabetic macular edema by administering to a subject an effective amount of one or more of the disclosed compounds or pharmaceutically acceptable salts, or formulations thereof. One embodiment of this aspect relates to a method for treating diabetic macular edema by administering to a subject a composition of: a) an effective amount of one or more of the disclosed compounds or pharmaceutically acceptable salts, and/or formulations thereof, and b) one or more carriers or compatible excipients.

Kits

Also disclosed are kits of the disclosed compounds and compositions for drug delivery into a human, mammal, or cell. The kits can comprise one or more packaged unit doses of a composition comprising one or more compounds to be delivered into a human, mammal, or cell. The unit dosage ampoules or multi-dose containers, in which the compounds to be delivered are packaged prior to use, can comprise a hermetically sealed container enclosing an amount of the active agent or pharmaceutically acceptable salt, or formulation thereof, suitable for a pharmaceutically effective dose thereof, or multiples of an effective dose. The compounds can be packaged as a sterile formulation, and the hermetically sealed container is designed to preserve sterility of the formulation until use.

The kit of the current invention has a single-use eye drop dispenser bottle for delivery of ophthalmic formulation. In an alternative embodiment, the kit of the current invention has a multi-use eye-drop dispenser bottle. The multi-dose dispenser bottle has appropriate amount of anti-infective and/or preservative agent, for example without being limited to, 0.005% BAK. The ophthalmic dispenser of the current invention has a top and a cap. The container of the current invention has a semi-transparent LDPE ophthalmic dispenser bottle with a LDPE dropper tip and HDPE cap. The container may be of other type and form as needed and/or as used in the art.

The following examples are illustrative, but not limiting, of the methods and compositions of the present invention. Other suitable modifications and adaptations of the variety of conditions and parameters normally encountered in therapy and that are obvious to those skilled in the art are within the spirit and scope of the embodiments.

EXAMPLES

Compound-I is a potent and selective small molecule inhibitor of VEGFR-2, along with other proangiogenic RTKs such as the FGF receptors (FGFR-1-3), Tie-2, and the ephrin receptor B4 (EPHB-4). Compound-I was shown to inhibit phosphorylation of specific RTKs, endothelial cell proliferation, and pathologic angiogenesis following systemic administration in murine cornea and rat growth plate models, as well as the growth of human tumor xenografts in athymic mice. Regarding potential ophthalmic indications, the Examples of the current invention described below demonstrated that topical ocular delivery of Compound-I provided significant inhibition of pathologic retinal and choroidal neovascularization in clinically-relevant rodent models. A summary of these data follows.

The following studies were conducted to measure the effect of the disclosed compounds on vascular leak and neovascularization of retina tissue.

Example 1

Primary Pharmacodynamics

In Vitro Efficacy Pharmacology of Compound-I. Compound-I potently inhibits the tyrosine kinase activity of vascular endothelial growth factor receptor-2 (VEGF-2), as well as a select subset of other proangiogenic RTKs, during various in vitro assays. Specifically, Compound-I compound blocked VEGF-stimulated VEGFR-2 phosphorylation in whole cells along with the proliferation of cultured endothelial cells. Compound-I inhibited recombinant tyrosine kinase activity of VEGFR-2 and FGFR-2 with a 50% inhibitory concentration ($IC_{50}$) of 10.55 nM (6 ng/mL) and 8.79 nM (5 ng/mL), respectively, and inhibited VEGFR-2 autophosphorylation in intact cells with an $IC_{50}$=5.27 nM (3 ng/mL). This inhibition was selective versus many other tyrosine kinases, e.g., the VEGFR-2 $IC_{50}$ was approximately 500× and 1000× lower than those for epidermal growth factor receptor (EGFR) and the insulin receptor (IR) tyrosine kinases, respectively (see Table 2).

When using a 10-point titration curve that ranged from 257 to 5000 nM (146-2845 ng/mL), Compound-I exhibited potent inhibition of tyrosine kinase activity for several proangiogenic growth factor receptors, as evidenced by an $IC_{50}$<100 nM (56.89 ng/mL) (see Table 3). The $IC_{50s}$ for this select group of kinases were as follows: recombinant KDR (human isoform of VEGFR-2)=1.27 nM (0.72 ng/mL), Tie-2=10.10 nM (5.75 ng/mL), and FGFRs 1-3=8.50 nM (4.84 ng/mL), 3.08 nM (1.75 ng/mL), and 33.9 nM (19.29 ng/mL), respectively. The compound also blocked the other high-affinity VEGF receptor, VEGFR-1/Flt-1, but with lower potency: $IC_{50}$=122 nM (69.41 ng/mL).

Although VEGFR inhibition appears to be essential for reducing vascular permeability and preventing further neovascular growth, the simultaneous inhibition of VEGF signaling with inhibition of other growth factor signaling pathways (e.g., PDGF and angiopoietins/Tie2) may be linked to unique therapeutic outcomes. The therapeutic outcomes of a broader inhibition of signaling pathways may contribute to the regression of newly established pathologic vessels in the posterior segment of the eye.

300 nM (170.67 ng/mL) of Compound-I completely inhibited VEGFR-2 kinase function (see Table 4) and provided substantial blockade of a similar set of proangiogenic growth factor receptors, including FGFRs-1-3, Tie-2, and EphB-4. An unexpected finding was that the 300 nM concentration was able to completely inhibit the VEGFR-2 kinase function. This concentration falls within the typical range found in the central choroid and retina following five days of topical ocular delivery in rabbits and dogs.

Overview of Drug Substance and Drug Product

Drug Substance: The active pharmaceutical ingredient (API), Formula II Hydrochloride (Compound-I, CP-547, 632-01), is a small molecule of a single polymorph. The API substance is consistently manufactured in purity exceeding 99.7%. Any impurity in drug substance ≥0.15% is suitably qualified in toxicology studies and the current specification for new unknown individual impurities is set to NMT 0.2%. The final drug substance and drug product are analyzed using standard methods.

Drug Product: Compound-I ophthalmic formulations for clinical studies was manufactured in dosage strengths between 0.05%-1.0% (as Compound-I). The strengths used for the GLP batches are 0% (placebo), 0.05%, 0.1%, 0.2%, 0.3%, 0.4%, 0.6%, 0.8%, and 1.0% Compound-I. Compound-I ophthalmic formulations (solutions or suspensions) are used for daily, single use, topical administration to the eye in the clinical trial. In addition to the active ingredient, the drug product contains 0.005% BAK as a preservative, purified water as vehicle, and is pH-adjusted with sodium hydroxide to pH 6.0.

Example 2

Sodium Phosphate-Based Gel Drop

The ophthalmic benefits of Compound-I in a sodium phosphate-based formulation (listed in Table 6) results from the self-gelling properties of the API in buffers, such as sodium phosphate. Spontaneous formation of a self-forming, thixotropic gel of Compound-I from a clear solution was formed by increasing API concentration in sodium phosphate. This gel initially appeared clear and then demonstrated increased thickness/viscosity at higher API concentrations, as well as becoming increasingly more opaque, i.e., turbid. Once the API concentration in the phosphate buffer reached super-saturated state, insoluble particulates of Compound-I also were observed within the gel.

Application of a gel with increased viscosity to the surface of the eye increases corneal residence time. Increased corneal residence time in turn facilitates ocular drug absorption. As a result, the intraocular drug concentrations of viscous gels increase in comparison to non-viscous formulations, such as water-like solutions. One way to increase viscosity is to use various viscosity-enhancing excipients, e.g., carboxymethylcellulose, which in effect achieves increased intraocular absorption of different drug substances following topical ocular administration. In this study, however, a thixotropic gel of Compound-I was unexpectedly formed in the absence of any viscosity-enhancing excipients. For example, when Compound-I was dissolved into a simple buffer, such as sodium phosphate, a thixotropic gel was formed. The thixotropic gel, which was formed without any viscosity-enhancing excipients, was formulated as a Gel Drop in this Example.

The Gel Drop of Compound-I was applied to eyes of Dutch-belted rabbits. Gel Drops of Compound-I were administered to Dutch-Belted rabbits for 4 or 5 consecutive days, with three times daily dosing. The concentrations of Compound-I at the target tissues were measured at 1 hour following the last administered dose. Delivery of Compound-I to the posterior segment tissues was dose-dependent and dose-frequency dependent.

The Gel Drop formulations (listed in Table 6) differed in several aspects, such as API concentration, sodium phosphate concentration, presence or absence of tonicity (glycerin) or preservative (benzalkoniumchloride/BAK) agents, solubilizing surfactants (polysorbate 80, tyloxapol, and/or poloxamer), and pH.

Example 3

Tromethamine-Based Suspension

Compound-I (about 1 mg/mL to about 10 mg/mL) in a tromethamine-based formulation formed a suspension. The suspension of Compound-I in a tromethamine-based formulation had >95% of the active drug substance in an insoluble form. This characteristic is distinguishable from the soluble or semi-soluble state of Compound-I in the Gel Drop (the Gel Drop (gel) is not an entirely soluble state as concentration of the active agent increases) or in a Cyclodextrin-based formulation. Tromethamine-based formulations of Compound-I showed increased turbidity with increasing active agent concentration. Administering a topical drop of Compound-I suspension to the eye (which is a combination of soluble and insoluble active agent components) was expected to provide unique benefits relevant to both safety/tolerability and efficacy.

Tromethamine-based suspension of Compound-I was administered to Dutch-Belted rabbits for 4 or 5 consecutive days with three times daily dosing. Ocular tissue and plasma concentrations of Compound-I were measured at 1 hour following the last administered dose. Compound-I in the tromethamine-based suspension delivered concentrations to the target tissues between 10-1000× of its cellular $IC_{50}$ for the various pro-angiogenic RTKs. See Table 7.

The corneal safety and tolerability of topical Compound-I was a direct consequence of the amount of soluble (as opposed to insoluble) active agent applied to the corneal surface, and the resultant corneal tissue concentration. Animals that received topical ocular administration of the tromethamine-based suspension were able to tolerate up to higher level of the active agent concentration in the formulation, as compared to equimolar formulations of the sodium phosphate-based Gel Drop. Results obtained from both Dutch-belted rabbits and beagle dogs suggested that ocular side effects, such as discomfort and inflammation and in some cases, corneal thinning, were more consistently observed when the cornea concentration of Compound-I exceeded 100 µM.

Administration of the tromethamine-based suspension had the unexpected effect on the ocular bioavailability of Compound-I in the posterior segment. The ocular bioavailability of Compound-I in the posterior segment was observed to be directly proportional to the total amount of drug administered (insoluble plus soluble, see Table 7). Although the insoluble drug particulates were not readily available to anterior segment tissues; the inherent and unique physicochemical properties of Compound-I allowed both insoluble and soluble components to gain entry to posterior segment tissues, such as the choroid and retina. Consequently, even higher drug concentrations than those achieved with Gel Drop formulations containing equivalent amounts of the active agent were achieved with the tromethamine-based suspension. Thus, tromethamine-based suspension provided: a) improved corneal tolerability and b) increased bioavailability to the posterior segment, particularly to the choroid, the primary target tissue for treating neovascular (wet) AMD.

Example 4

Cyclodextrin-Based Solution

Cyclodextrins, which are cyclic oligosaccharides made up of six to eight dextrose units (α-, β-, and γ-CDs) joined through one to four bonds, are well-known for their ability to act as a solubilizing agent for relatively insoluble drugs. See Stella & He, Cyclodextrins, *Toxicol. Pathol.*, 36: 30-42 (2008).

A clinical formulation of Compound-I or its free base ophthalmic Solution in 2-hydroxypropyl-β-cyclodextrin (HP-β-CD, KLEPTOSE® HPB) at equal to or more than 1:6 molar ratio or Sulfobutylether-β-cyclodextrin (SBE-β-CD, CAPTISOL®) at β at equal to or more than 1:2 ratio provided solubility with clinical dose strengths of 0.1-1.0% Compound-I.

Cyclodextrin-based solutions of Compound-I or its free base not only improved solubility of the active agent into a uniform solution, but, upon topical ocular administration, also had a novel and previously unobserved characteristic of significantly increased therapeutic index of the active agent at the posterior segment of the eye. The solution reduced anterior segment exposure, thereby providing increased concentration of the active in the solution and increased delivery frequency, which maintained high posterior segment concentrations. Both of these beneficial characteristics are related to the known property of cyclodextrin to form hydrophilic complexes with hydrophobic drugs. See Stella & He, Cyclodextrins, *Toxicol. Pathol.*, 36: 30-42 (2008). When formulated with Compound-I or its free base, cyclodextrin formed a clear, colorless solution and exhibited water-like viscosity. Following topical ocular administration, the Compound-I/cyclodextrin complex had the appearance of being pharmacologically inactive and metabolically inert. The Compound-I/cyclodextrin complex conferred corneal tolerability until cyclodextrin spontaneously dissociated from the active agent, thus making available high concentration of Compound-I at its intended site of action in the posterior segment of the eye, e.g., choroid and retina.

During topical ocular dosing studies lasting from 1 to 30 days in Dutch-belted rabbits, cyclodextrin-based solutions of Compound-I demonstrated dramatically lowered corneal exposures compared to Gel Drop formulations (see Example 2) at similar drug concentrations. The use of cyclodextrin-based solutions of Compound-I provided an approximate 10× reduction in corneal concentrations, as compared to dosing with equimolar formulations of the Gel Drop. Consequently, after 30 days of topical ocular dosing of 0.6% Compound-I as a cyclodextrin-based solution, no untoward findings were attributed to test-article or vehicle. The cyclodextrin-based solution of Compound-I also achieved equal or significantly higher concentrations of drug within the posterior segment target tissues, such as at the central choroid and the central retina. The combined effects of decreasing corneal drug exposure so as to avoid poor ocular tolerability, while increasing posterior segment bioavailability so as to increase RTK inhibition, may significantly increase the therapeutic index and corresponding benefit(s) experienced by patients.

For both suspension-based formulations (see Example 3) and the cyclodextrin formulations, the therapeutic window is expanded due to significantly reduced exposure (10-100× or 1-2 log reduction). The reduced exposure improves corneal safety/tolerability, which allows higher concentrations or frequency of dosing of Compound-I to be administered topically. The higher concentrations enables the drug to achieve higher back of the eye target tissue concentrations, which improves the therapeutic efficacy of Compound-I.

This study demonstrated that in rabbits and dogs, topical ocular dosing of ophthalmic gel drops, was associated with high corneal tissue exposure (≥100 uM) and corresponding untoward observations in the anterior segment, such as discomfort, corneal and conjunctival inflammation, corneal epithelial erosion and/or thinning and degeneration. In contrast, repeated topical ocular dosing of Compound-I ophthalmic solution produced corneal exposure that are roughly 5 to 10-fold lower than an equimolar dose of ophthalmic gel drops, and are free of untoward clinical or histopathologic findings. Furthermore, topical ocular dosing with Compound-I ophthalmic solution achieved equal or higher target therapeutic exposure in the central choroid in comparison to an equimolar dose of the ophthalmic gel drop. Overall, the combination of decreased corneal exposure and corresponding improved ocular tolerability, while simultaneously maintaining or promoting drug delivery to the posterior segment target tissues, along with improved physicochemical stability, will provide greater benefit to patients compared to the ophthalmic Gel Drop formulation.

Example 5

1- to 5-Day PK Results with Topical Ocular Compound-I in Cyclodextrin-Based Solutions Following topical ocular dose administration of various formulations and dosage regimens of Compound-I in Dutch Belted rabbits, ocular pharmacokinetics was investigated. Nine (9) different topical ocular formulations having three doses of Compound-I were administered either once per day (q.d.) or twice per day (b.i.d.) for 1, 4, or 5 consecutive days. The study design (see Tables 10A-C) consisted of seventy-two (72) rabbits each receiving a 30 µL bilateral topical ocular dose of one of three (3) Compound-I formulations, or vehicle formulation, using a positive displacement pipette.

The composition of each Compound-I formulation is described in Table 8A. All doses were administered within ±1 hour of the scheduled dose time. On day 1, Groups 1, 2, 4-6, 8, 10, 11, 13, 15, and 17 received one dose (q.d.) for either one (1) or four (4) days. On days 1 through 4, Groups 3, 7, 9, 12, 14, and 16 received b.i.d. dosing approximately 8 hours apart at 7:00 AM and 3:00 PM for four (4) days. Animals in Groups 18 and 19 received b.i.d dosing of vehicle only formulations for five (5) consecutive days.

Ocular sampling occurred for Group 1 at 0.5, 1, 2, 4, 8, or 24 hours post-dose relative to the day 1 dose. Ocular sampling occurred for Groups 2 and 6 at 1, 8, and 24 hours post-dose relative to the day 5 morning dose. Ocular sampling for Groups 3, 7, 8, 11, and 13 occurred at 1 and 24 hours post-dose relative to the day 5 morning dose. Ocular sampling for Groups 4, 9, 10, 12, 14, 15, 16, and 17 occurred at 1 hour post-dose relative to the day 5 morning dose. Group 5 ocular sampling occurred at 0.5, 1, 2, 4, 8, and 24 hours post-dose relative to the day 1 dose. Animals in Groups 18 and 19 were followed only by clinical observations for five (5) days.

Aqueous humor, cornea, central and peripheral retina, and central and peripheral choroid samples were collected. Aqueous humor, cornea, central retina, and central choroid samples were then assayed. Peripheral retina and peripheral choroid samples were assayed only for Groups 1-8, 12, 14, and 16 per study protocol.

Rabbit aqueous humor, cornea, central and peripheral retina, and central and peripheral choroid samples were analyzed. Calibration curves were prepared in control matrix to determine the concentration of Compound-I in the various tissues.

Example 6

5-Day PK Results with Topical Ocular Compound-I in Cyclodextrin-Based Solutions

Following ocular dose administration of various dose regimens of topical ocular solutions of Compound-I containing hydroxypropyl-β-cyclodextrin ("HDβCD") in Dutch-Belted rabbits, the ocular pharmacokinetics was calculated. Nine (9) different topical ocular solutions having four different doses of Compound-I were administered either once per day (q.d.) or twice per day (b.i.d.) for either 4 or 5 consecutive days. The study design consisted of forty (40) rabbits each receiving a 30 µL bilateral topical ocular dose of one of four (4) Compound-I dosage strengths, using a positive displacement pipette.

All doses were administered with ±1 hour of the scheduled dose time, except on day 1 for Groups 1, 4, and 10. The first dose on day 1 was administered at 12:00 PM, and the second dose (for Groups 1 and 10) was administered approximately 4 hours after. This was due to delayed arrival of formulations. All other dosing for these groups was as scheduled. On day 1, Groups 4-8, and 11-12 received one dose (q.d.) for four (4) days. On days 1 through 4, Groups 1-3, and 9-10 received b.i.d. dosing approximately 8 hours apart for four (4) days.

Ocular sampling occurred one hour following the first daily dose on day 5 for all groups, except Groups 5b and 6b, where ocular sampling occurred 24 hours after the first daily dose on day 4.

Blood samples for plasma collection were obtained just prior to scheduled euthanasia for all animals. Aqueous humor, cornea, central and peripheral retina, and central and peripheral choroid samples were collected. Cornea, central retina, and central choroid samples from groups 1-12 were assayed. Aqueous humor, peripheral retina, and peripheral choroid samples were not assayed.

Example 7

Concentrations of Compound-I (in µM) in Various Ocular Fluids and Tissues

The ocular solution of Compound-I comprising cyclodextrin was prepared and tested in different groups of animals. Upon topical ocular administration of a solution of 0.4% (4 mg/mL) Compound-I and cyclodextrin, the concentration of the active agent was measured in various tissues and fluids of the eye. Average concentration of Compound-I was measured in the central choroid, central retina, aqueous humor, and cornea. Compound-I was in a solution (0.4% or 4 mg/mL) with 8.41% KLEPTOSE® and 0.142% phosphate buffer; 8.9% KLEPTOSE® HPB and 0.142% phosphate; 4.88% CAPTISOL® and 0.142% phosphate; or 4.88% CAPTISOL® and 0.122% phosphate. See Table 10A-B.

The central choroid concentration of Compound-I was between 0.259 µM and 0.769 µM. See Table 10A. The central retina concentration of Compound-I was between 0.0531 µM-0.124 µM. See Table 10A. The aqueous humor concentration of Compound-I was between 0.00313 µM-0.00656 µM. See Table 10A. And the corneal concentration of Compound-I was 6.49 µM-30 µM. See Table 10A. The cyclodextrins used to prepare the solutions were KLEPTOSE® HPB or CAPTISOL®. See Table 10B.

Example 8

Ocular Toxicology Studies

Dose-limiting ocular toxicity was characterized by corneal and conjunctival findings in Dutch-Belted rabbits and beagle dogs. These ocular findings from repeat-dose toxicology studies with Compound-I ophthalmic gel drops were based upon clinical ophthalmic and histopathologic evaluations and limited to conjunctival hyperemia, chemosis, congestion, and discharge, corneal opacification and epithelial erosion, and keratoconjunctivitis. No untoward alterations involving deeper structures of the eye (iris, lens, ciliary body, retina, choroid, sclera) or the optic nerve were observed. Retinal function was normal in all test article and vehicle treated groups during full-field electroretinograms performed in rabbits.

The objectives for the exploratory ocular toxicology studies were to identify: a) a topical ocular formulation that was well tolerated and b) one that could achieve the targeted therapeutic concentrations of Compound-I in the central choroid.

Mean Compound-I ocular tissue concentrations following twice daily topical dosing with 0.3% Compound-I ophthalmic gel drop formulations with and without benzylalkonium chloride were highest in the cornea (236-260 µM)>>peripheral choroid (2.79-4.10 µM), central choroid (0.340-0.496 µM), peripheral retina (0.150-0.3091 µM) and aqueous humor (0.0197-0.0395 µM) in Dutch-Belted rabbits.

Tris-based suspension formulations were well tolerated, where clinical ophthalmic examinations revealed a notable absence of corneal findings with only a few sporadic incidences of mild conjunctivitis in Dutch-Belted rabbits. Moreover, the eyes from animals that had received 0.3% w/v Compound-I Tris-based suspension twice daily for 30 days were considered normal during microscopic evaluations. Mean Compound-I ocular tissue concentrations, assessed at 1 hour±15 minutes after the first daily topical ocular dose on day 30 for the twice daily topical dosing with 0.3% Compound-I Tris-based suspensions with and without benzylalkonium chloride, were highest in the cornea (2.69-3.10 µM)>>peripheral choroid (0.781-1.21 µM), central choroid (0.303-0.319 µM), peripheral retina (0.0819-0.0868 µM), central retina (0.0495-0.0592 µM), and aqueous humor (0.00127-0.00145 µM).

Cyclodextrin-based solutions, using hydroxypropyl-beta-cyclodextrin (HP-n-CD, KLEPTOSE® HPB), were well tolerated when administered topically for 30 days, twice daily at 0.1% Compound-I (2.1% HP-β-CD), twice daily at 0.2% Compound-I (4.21% HP-β-CD), once or twice daily at 0.4% Compound-I (8.41% HP-β-CD), and once or twice daily at 0.6% Compound-I (up to 12.62% HP-β-CD) in Dutch-Belted rabbits. Moreover, in a similar repeat dosing study, cyclodextrin-based solutions of 0.4% w/v Compound-I in KLEPTOSE® HPB, KLEPTOSE® HP, or CAPTISOL® were well-tolerated when dosed twice daily for 24 days. No overt ocular toxicity related to Compound-I or vehicle treatment was found during clinical ophthalmic or microscopic examinations in either study.

In the 24-day study, ocular tissue concentrations from eyes treated with cyclodextrin-based solutions of Compound-I were assessed at 1 hour±15 minutes after the first daily topical ocular dose on day 24 were in descending order highest in the cornea (6.49-30 µM)>>center-punch choroid (0.212-0.769 µM)>center-punch retina (0.0531-0.124)>aqueous humor (0.002-0.007).

In summary, dose-limiting corneal toxicity was observed with Compound-I ophthalmic Gel Drop formulations. The ophthalmic Gel Drop renders five-fold to fifteen-fold higher corneal concentrations of Compound-I compared to cyclodextrin based solution, and fifty-fold to hundred-fold higher corneal concentrations of Compound-I compared to Tris-based suspensions. Compound-I Tris-based suspensions and cyclodextrin-based solutions were well tolerated with no evidence of overt ocular toxicity. Dose levels that were well tolerated for the cyclodextrin-based solutions or Tris-based suspensions of Compound-I when administered once or twice daily ranged from about 0.005% to about 5.0% w/v for at least 30 days. Cyclodextrin-based solutions also provided the highest central choroid concentrations of Compound-I when using equimolar doses of the three formulations, and met or exceeded target therapeutic concentrations.

Example 9

Phase I Protocol for Dose-Escalation Study in Patients with Neovascular AMD

The Phase I study is a twelve-week, open-label, dose-escalating, multi-center trial designed to evaluate the safety, tolerability, and pharmacokinetics following topical ocular administration of Compound-I in patients with neovascular age-related macular degeneration (AMD). Up to 60 patients total are treated one to two times daily with topical ocular dosing of Compound-I ophthalmic solution for three months, where three dose-escalating monotherapy arms and one adjunct therapy arm using a single intravitreal injection of LUCENTIS® plus the maximally-tolerated monotherapy dose are planned (15 patients per treatment arm). Patients that meet pre-specified vision and CNV lesion criteria confirmed by an independent reading center are allowed to simultaneously discontinue topical ocular dosing and receive treatment with standard-of-care.

Compound-I ophthalmic solution for clinical studies is manufactured in at least 3 dosage strengths, ranging from 0.1% to 1.0% (as Compound-I). The strengths for the GLP batches are 0% (placebo), 0.1%, 0.3%, 0.6%, and 1.0% Compound-I HCl. Up to 2- to 3-fold incremental doses (approximately ½ log unit steps) are administered to succeeding cohorts.

Example 10

A "non-gel," "non-viscous," homogeneous ophthalmic solution topical formulation that is both physically and chemically stable over the drug strengths of 0.1-1.0% (1 to 10 mg/ml) was prepared by measuring the Compound-I concentration, cyclodextrin complexing agent concentration, pH, and tonicity, on Compound-I solubility and stability. A suitable buffering system prevents pH drift on stability at concentrations less than 1 mg/mL. Both phosphate and Trometamol (Tris) were evaluated as buffering agents. Sodium chloride was used to adjust tonicity.

The product quality attributes are shown in Table 14.

TABLE 14

| Product Quality Attributes | |
| --- | --- |
| Solvent | Solubility (mg/mL) |
| Color Appearance of formulation | Clear colorless with no visually apparent |
| pH | pH 5.5-7.0 |
| Turbidity | Clear |
| Viscosity | Free flowing, water-like and filterable |

TABLE 14-continued

| Product Quality Attributes | |
| --- | --- |
| Solvent | Solubility (mg/mL) |
| Tonicity | Isotonic |
| Sedimentation | None |
| Mixing end point | Clear colorless with no visually apparent |
| Solubility | Solubility ≥ 6 mg /ml |

Formulation Preparation

The formulations outlined in Tables 12 and 13 were prepared using the general procedure listed.

The formulation was made up to volume with water for injection and stirred for 30 minutes at 500 rpm. Final pH was checked and adjusted with either, NaOH or HCl to the target range. Approximately 5 ml aliquots is directly filtered into semi-transparent 5 ml LDPE bottles while continuously stirring at constant speed with the aid of Watson Marlow Pumpsil D tubing, fitted to a Flexicon filler and attached to 0.2 micron PVDF capsule filter. Samples are stored at 2-8° C. until all sample preparation is complete. All samples will then be submitted to analytical for storage and testing.

INCORPORATION BY REFERENCE

The entire disclosure of each of the patent documents and scientific articles referred to herein is incorporated by reference for all purposes. In the present disclosure the host document is identified with sufficient particularity and materials that are relevant to the disclosure is construed based on the context of the reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and the foregoing description and examples are for purposes of illustration and not limitation of the claims that follow.

EQUIVALENTS

The invention can be embodies in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A topical, ocular suspension formulation, comprising:
a. solid particles of an active agent of Formula II:

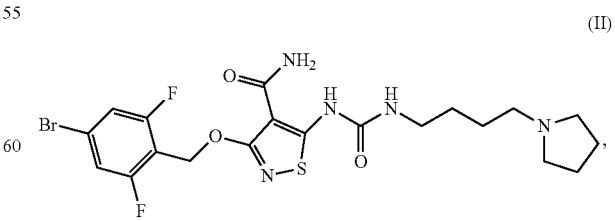

(II)

or a pharmaceutically acceptable salt thereof, and
b. pharmaceutically acceptable excipients;
wherein the active agent or the pharmaceutically acceptable salt is present in about 0.005% to about 5.0% w/v.

2. The formulation of claim 1, further comprising a solubilizing agent.

3. The formulation of claim 2, wherein the solubilizing agent is cyclodextrin selected from the group consisting of 2-hydroxypropyl-β-cyclodextrin, methyl-β-cyclodextrin, randomly methylated-β-cyclodextrin, ethylated-β-cyclodextrin, triacetyl-β-cyclodextrin, peracetylated-β-cyclodextrin, carboxymethyl-β-cyclodextrin, hydroxyethyl-β-cyclodextrin, 2-hydroxy-3-(trimethylammonio)propyl-β-cyclodextrin, glucosyl-β-cyclodextrin, maltosyl-β-cyclodextrin, sulfobutyl ether-β-cyclodextrin, branched-β-cyclodextrin, hydroxypropyl-γ-cyclodextrin, randomly methylated-γ-cyclodextrin, trimethyl-γ-cyclodextrin, and combinations thereof.

4. The formulation of claim 1, wherein the pharmaceutically acceptable salt is a hydrochloride salt provided by the formula:

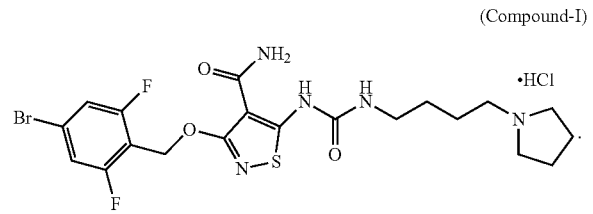 [SMILES: NC(=O)c1c(OCc2c(F)cc(Br)cc2F)nsc1NC(=O)NCCCCN1CCCC1 ; Cl]

(Compound-I)

5. The formulation of claim 3, wherein the solubilizing agent is 2-hydroxypropyl-β-cyclodextrin or β-cyclodextrin sulfobutyl ether.

6. The formulation of claim 1, comprising about 0.005%, about 0.05%, about 0.1%, about 0.2%, about 0.3%, about 0.4%, about 0.5%, about 0.6%, about 0.7%, about 0.8%, about 0.9%, about 1.0%, about 2.0%, about 3.0%, about 4.0%, or about 5.0% w/v of the active agent or a pharmaceutically acceptable salt thereof.

7. The formulation of claim 1, further comprising one or more of benzalkonium chloride (BAK), sodium chloride, and a pH adjusting agent.

8. The formulation of claim 1, comprising about 0.005%, about 0.05%, about 0.1%, about 0.2%, about 0.3%, about 0.4%, about 0.5%, about 0.6%, about 0.7%, about 0.8%, about 0.9%, about 1.0%, about 2.0%, about 3.0%, about 4.0%, or about 5.0% w/v of the active agent or a pharmaceutically acceptable salt thereof, and about 0.3%-about 1% w/v tromethamine.

9. The formulation of claim 1, comprising about 0.005%, about 0.05%, about 0.1%, about 0.2%, about 0.3%, about 0.4%, about 0.5%, about 0.6%, about 0.7%, about 0.8%, about 0.9%, about 1.0%, about 2.0%, about 3.0%, about 4.0%, or about 5.0% w/v of the active agent or a pharmaceutically acceptable salt thereof, about 0.3%-about 1% w/v tromethamine, and about 0.005% w/v benzalkonium chloride (BAK).

10. The formulation of claim 1, having a pH value of about 4.5 to about 7.5 at or under about 40° C.

11. The formulation of claim 1, having a pH value of about 6.0 at or under about 40° C.

12. The formulation of claim 1, having a pH value of about 5.0 to about 7.0 at or under about 40° C.

13. The formulation of claim 1, wherein the formulation is suitable for accessing posterior segment of the eye and/or for treating and/or ameliorating ocular neovascularization.

14. A method for treating and/or ameliorating a posterior segment disease of the eye, comprising administering to a subject in need thereof the formulation of claim 1, wherein the disease is selected from the group consisting of: diabetic retinopathy, age-related macular degeneration (AMD), pathologic choroidal neovascularization (CNV), pathologic retinal neovascularization, uveitis, retinal vein occlusion, ocular trauma, surgery induced edema, surgery induced neovascularization, cystoid macular edema, ocular ischemia, retinopathy of prematurity, Coat's disease, sickle cell retinopathy, and neovascular glaucoma.

15. The method of claim 14, wherein the diabetic retinopathy is background diabetic retinopathy, proliferative diabetic retinopathy, or diabetic macular edema.

16. The method of claim 14, wherein the AMD is neovascular AMD, dry AMD, or Geographic Atrophy.

17. The method of claim 16, wherein the neovascular AMD is wet or exudative AMD.

18. The method of claim 14, wherein the CNV is related to high myopia, trauma, sickle cell disease, ocular histoplasmosis, angioid streaks, traumatic choroidal rupture, drusen of the optic nerve, or retinal dystrophies.

19. The method of claim 14, wherein the pathologic retinal neovascularization is related to sickle cell retinopathy, Eales disease, ocular ischemic syndrome, carotid cavernous fistula, familial exudative vitreoretinopathy, hyperviscosity syndrome, idiopathic occlusive arteriolitis, birdshot retinochoroidopathy, retinal vasculitis, sarcoidosis, or toxoplasmosis.

20. The method of claim 14, wherein retinal vein occlusion is central or branch occlusion.

21. The formulation of claim 1, wherein the pharmaceutically acceptable excipient is selected from hydroxy propyl methyl cellulose (HPMC) and carboxylmethyl cellulose and salts thereof.

22. The formulation of claim 1, further comprising a nonionic liquid polymer of the alkyl aryl polyether alcohol type.

23. The formulation of claim 22, wherein the nonionic liquid polymer of the alkyl aryl polyether alcohol type is tyloxapol.

24. The formulation of claim 1, further comprising a hydrophilic non-ionic surfactant.

25. The formulation of claim 24, wherein the hydrophilic non-ionic surfactant is poloxamer.

26. The formulation of claim 25, wherein the poloxamer is poloxamer 407.

27. A topical, ocular, suspension formulation, comprising: solid particles of an active agent of Formula II:

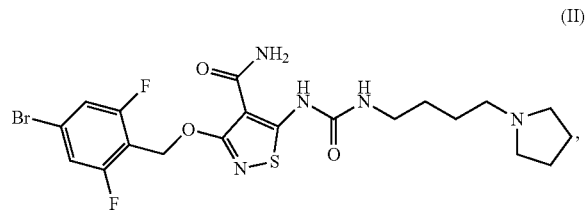 [SMILES: NC(=O)c1c(OCc2c(F)cc(Br)cc2F)nsc1NC(=O)NCCCCN1CCCC1]

(II)

or a pharmaceutically acceptable salt thereof,
pharmaceutically acceptable excipients selected from hydroxy propyl methyl cellulose (HPMC) and carboxylmethyl cellulose and salts thereof, and
a nonionic liquid polymer of the alkyl aryl polyether alcohol type,
wherein the active agent or the pharmaceutically acceptable salt is present in about 0.005% to about 5.0% w/v.

28. The formulation of claim 27, wherein the active agent is present in about 0.1% to about 2.0% w/v.

29. The formulation of claim 27, wherein the pharmaceutically acceptable salt is a hydrochloride salt of the formula:

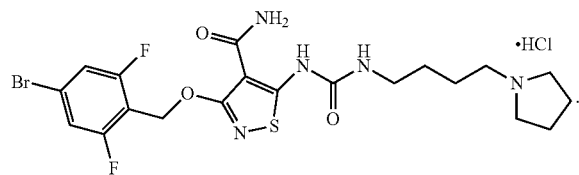 [SMILES: NC(=O)c1c(OCc2c(F)cc(Br)cc2F)nsc1NC(=O)NCCCCN1CCCC1 ; Cl]

30. The formulation of claim 27, wherein the nonionic liquid polymer of the alkyl aryl polyether alcohol type is tyloxapol.

31. The formulation of claim 27, further comprising a hydrophilic non-ionic surfactant.

32. The formulation of claim 31, wherein the hydrophilic non-ionic surfactant is poloxamer.

33. The formulation of claim 32, wherein the poloxamer is poloxamer 407.

34. A topical, ocular, suspension formulation, comprising: solid particles of an active agent of Formula II:

(II)

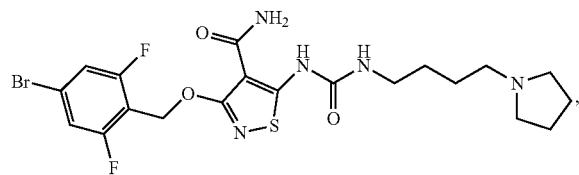

or a pharmaceutically acceptable salt thereof, pharmaceutically acceptable excipients selected from hydroxy propyl methyl cellulose (HPMC) and carboxylmethyl cellulose and salts thereof, and about 0.3%-1% w/v tromethamine,
about 2% glycerin,
tyloxapol, and
poloxamer, wherein the active agent or the pharmaceutically acceptable salt is present in about 0.005% to about 5.0% w/v.

35. The formulation of claim 34, wherein the active agent is present in about 0.1% to about 2.0% w/v.

36. The formulation of claim 34, wherein the pharmaceutically acceptable salt is a hydrochloride salt of the formula:

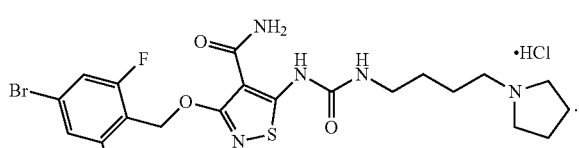

37. The formulation of claim 34, wherein the poloxamer is poloxamer 407.

* * * * *

UNITED STATES PATENT AND TRADEMARK OFFICE
CERTIFICATE OF CORRECTION

PATENT NO. : 10,307,404 B1  
APPLICATION NO. : 16/042003  
DATED : June 4, 2019  
INVENTOR(S) : David P. Bingaman et al.

Page 1 of 1

It is certified that error appears in the above-identified patent and that said Letters Patent is hereby corrected as shown below:

In the Claims

At Column 62, Claim number 1, Line number 53:
"A topical, ocular suspension formulation, comprising:"

Should read:
--A topical, ocular, suspension formulation, comprising:--

Signed and Sealed this  
Thirtieth Day of July, 2019

Andrei Iancu  
*Director of the United States Patent and Trademark Office*